US008338189B2

(12) United States Patent
Lin et al.

(10) Patent No.: US 8,338,189 B2
(45) Date of Patent: Dec. 25, 2012

(54) DETECTION OF BIOMARKERS AND BIOMARKER COMPLEXES

(75) Inventors: Yixin Lin, Stormville, NY (US); Jean-Francois Houle, Toronto (CA)

(73) Assignee: Axela Inc., Toronto (CA)

( * ) Notice: Subject to any disclaimer, the term of this patent is extended or adjusted under 35 U.S.C. 154(b) by 521 days.

(21) Appl. No.: 12/397,772

(22) Filed: Mar. 4, 2009

(65) Prior Publication Data

US 2009/0233268 A1   Sep. 17, 2009

Related U.S. Application Data

(60) Provisional application No. 61/068,265, filed on Mar. 5, 2008.

(51) Int. Cl.
*G01N 33/543* (2006.01)
(52) U.S. Cl. ........ 436/518; 435/7.1; 435/7.92; 436/501; 436/540
(58) Field of Classification Search ........................ None
See application file for complete search history.

(56) References Cited

U.S. PATENT DOCUMENTS

| | | | |
|---|---|---|---|
| 5,736,343 A * | 4/1998 | Landry .......................... | 435/7.6 |
| 5,795,725 A | 8/1998 | Buechler et al. | |
| 6,156,521 A | 12/2000 | Buechler et al. | |
| 6,991,907 B1 | 1/2006 | Buechler et al. | |
| 6,991,938 B1 | 1/2006 | Cookson et al. | |
| 7,008,794 B2 | 3/2006 | Goh et al. | |
| 7,098,041 B2 | 8/2006 | Kaylor et al. | |
| 7,102,752 B2 | 9/2006 | Kaylor et al. | |
| 7,118,855 B2 | 10/2006 | Cohen et al. | |
| 7,169,550 B2 | 1/2007 | Sayre et al. | |
| 7,214,530 B2 | 5/2007 | Sayre et al. | |
| 7,223,368 B2 | 5/2007 | Cohen et al. | |
| 7,223,534 B2 | 5/2007 | Kaylor et al. | |
| 7,244,393 B2 | 7/2007 | Kaylor et al. | |
| 7,314,749 B2 * | 1/2008 | Goh et al. ................... | 435/287.1 |
| 2003/0049693 A1 | 3/2003 | Goh et al. | |
| 2003/0092092 A1 * | 5/2003 | Pandak et al. ................ | 435/7.93 |
| 2006/0099649 A1 | 5/2006 | Goh et al. | |
| 2007/0154881 A1 | 7/2007 | Koo | |
| 2008/0153109 A1 * | 6/2008 | Eriksson et al. .............. | 435/7.1 |
| 2011/0111524 A1 * | 5/2011 | Goix et al. ................... | 436/501 |

FOREIGN PATENT DOCUMENTS

| | | |
|---|---|---|
| WO | WO 93/25910 | 12/1993 |
| WO | WO 97/26534 | * 4/1997 |

OTHER PUBLICATIONS

Altwegg et al., "Myeloid-related protein 8/14 complex is released by monocytes and granulocytes at the site of coronary occlusion: a novel, early, and sensitive marker of acute coronary syndromes," *Eur. Heart J.* 28(8): 941-948 (2007).
Borisenko et al., "Diffractive optics technology: a novel detection technology for immunoassays," *Clin. Chem.* 52(11): 2168-2170 (2006).
Cao et al., "Double-enhancement strategy: A practical approach to a femto-molar level detection of prostate specific antigen-alpha1-antichymotrypsin (PSA/ACT complex) for SPR immunosensing," *J. Microbiol. Biotechnol.* 17(6): 1031-1035 (2007).
Goh et al., "Diffraction-based assay for detecting multiple analytes," *Anal. Bioanal. Chem.* 374(1): 54-56 (2002).
HyTest Ltd., "Markers of Cardiovascular Diseases and Metabolic Syndrome," retrieved Jun. 6, 2012 from http://www.hytest.fi/catalogs.
Lin et al., "Development of a novel diffraction-based immunoassay for characterizing the primary and ternary structure of the circulating form of cardiac troponin," Poster presented on Jan. 29, 2010.
Lin et al., "Development of a qualitative sequential immunoassay for characterizing the intrinsic properties of circulating cardiac troponin I," *Clin. Chem.* 56(8): 1307-1319 (2010).
Un et al., "Intra-feature and inter-feature multiplexing using diffractive optics technology: more information from less sample," Poster presented at the 41st annual Oak Ridge Conference, Baltimore, MD, Apr. 16 & 17, 2009.
Morjana, "Degradation of human cardiac troponin I after myocardial infarction," *Biotechnol. Appl. Biochem.* 28: 105-111 (1998).
Ndao et al., "Rapid determination of Strongyloides infection using a novel diffractive optics technology," Poster presented on Sep. 26, 2009.
Extended European Search Report for European Patent Application No. 09716287, dated Jul. 19, 2011.
International Search Report for International Application No. PCT/US2009/001394, dated Oct. 27, 2009.

* cited by examiner

*Primary Examiner* — Melanie J Yu
*Assistant Examiner* — Gary W Counts
(74) *Attorney, Agent, or Firm* — Clark & Elbing LLP; Kristina Bicker-Brady

(57) ABSTRACT

The invention features methods and devices for the detection of biomarker complexes and their components and for the sequential detection of multiple epitopes of a biomarker. The invention also features methods for diagnosing disease and evaluating the efficacy of treatment of a subject with a disease.

15 Claims, 15 Drawing Sheets

Figure 13 (cont.)
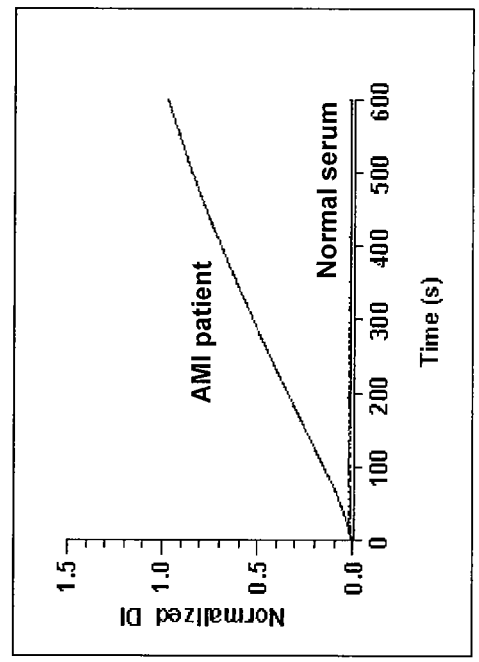
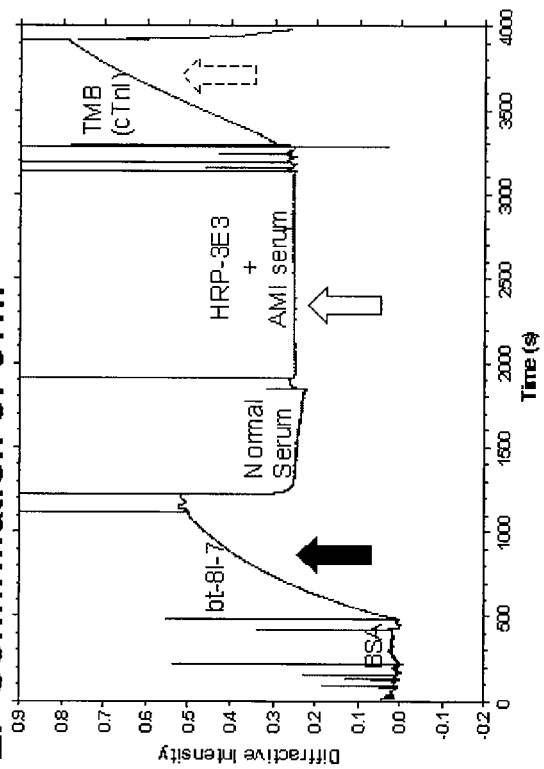

SEQUENCE LISTING

<160> NUMBER OF SEQ ID NOS: 1

<210> SEQ ID NO 1
<211> LENGTH: 210
<212> TYPE: PRT
<213> ORGANISM: Homo sapiens

<400> SEQUENCE: 1

Met Ala Asp Gly Ser Ser Asp Ala Ala Arg Glu Pro Arg Pro Ala Pro
1               5                   10                  15

Ala Pro Ile Arg Arg Arg Ser Ser Asn Tyr Arg Ala Tyr Ala Thr Glu
            20                  25                  30

Pro His Ala Lys Lys Lys Ser Lys Ile Ser Ala Ser Arg Lys Leu Gln
        35                  40                  45

Leu Lys Thr Leu Leu Leu Gln Ile Ala Lys Gln Glu Leu Glu Arg Glu
    50                  55                  60

Ala Glu Arg Arg Gly Glu Lys Gly Arg Ala Leu Ser Thr Arg Cys
65                  70                  75                  80

Gln Pro Leu Glu Leu Ala Gly Leu Gly Phe Ala Glu Leu Gln Asp Leu
                85                  90                  95

-continued

```
Cys Arg Gln Leu His Ala Arg Val Asp Lys Val Asp Glu Glu Arg Tyr
            100                 105                 110

Asp Ile Glu Ala Lys Val Thr Lys Asn Ile Thr Glu Ile Ala Asp Leu
            115                 120                 125

Thr Gln Lys Ile Phe Asp Leu Arg Gly Lys Phe Lys Arg Pro Thr Leu
            130                 135                 140

Arg Arg Val Arg Ile Ser Ala Asp Ala Met Met Gln Ala Leu Leu Gly
145                 150                 155                 160

Ala Arg Ala Lys Glu Ser Leu Asp Leu Arg Ala His Leu Lys Gln Val
                165                 170                 175

Lys Lys Glu Asp Thr Glu Lys Glu Asn Arg Glu Val Gly Asp Trp Arg
            180                 185                 190

Lys Asn Ile Asp Ala Leu Ser Gly Met Glu Gly Arg Lys Lys Lys Phe
            195                 200                 205

Glu Ser
    210
```

DETECTION OF BIOMARKERS AND BIOMARKER COMPLEXES

CROSS-REFERENCE TO RELATED APPLICATIONS

This application claims benefit of U.S. Provisional Application No. 61/068,265, filed Mar. 5, 2008, which is hereby incorporated by reference.

BACKGROUND OF THE INVENTION

In general, this invention relates to the fields of optical diffraction and biomarker detection.

Many biological molecules have been identified as biomarkers for the diagnosis of disease. Biomarkers of disease exist in biological fluids in the form of complexes, which are often heterogeneous in composition. The detection of these biomarker complexes and the determination of their composition often require large amounts of a biological sample in order to purify the complexes by traditional chromatographic means. In addition, traditional methodologies may require derivation of antibodies that are specific to the complexed or dissociated components of the biomarker complex.

Thus, there exists a need in the art for methods to detect, quantify, and characterize biomarkers and biomarker complexes for the detection and diagnosis of disease.

SUMMARY OF THE INVENTION

In general, the invention features methods, kits, and devices for the detection of biomarker complexes and their components and for the sequential detection of multiple epitopes of a biomarker. The invention also features methods for diagnosing disease and evaluating the efficacy of treatment of a subject with a disease.

Accordingly, in one aspect, the invention features a method of detecting a component of a biomarker complex in a biological sample by contacting the sample with a device so that the biomarker complex in the sample binds to a binding agent immobilized on a surface of the device in a pattern that generates a signal. The method also includes contacting the surface of the device with a first detecting binding agent that specifically binds to a first component of the biomarker complex and not to a second component of the biomarker complex and detecting the first component by a change in signal produced by the pattern upon binding of the first detecting binding agent to the first component.

In one embodiment, the method further includes contacting the surface with a second or further detecting binding agent that specifically binds to a second or further component of the biomarker complex and does not specifically bind to other assayed components.

In another aspect, the invention features a method of sequentially detecting at least three epitopes of a biomarker in a biological sample. The method includes contacting the biological sample with a device having an immobilized binding agent on its surface in a pattern that generates a signal so that the biomarker in the sample binds to the immobilized binding agent. The method further includes contacting the surface with first, second, and third detecting binding agents that specifically bind to first, second, and third epitopes of the biomarker; detecting the first epitope by a change in signal produced by the pattern upon binding of the first detecting binding agent to the first epitope; detecting the second epitope by a change in signal produced by the pattern upon binding of the second detecting binding agent to the second epitope; and detecting the third epitope by a change in signal produced by the pattern upon binding of the third detecting binding agent to the third epitope. The first, second, and third detecting binding agents may be contacted with the sample at the same time or sequentially, depending on the detection. Preferably, the detecting binding agents are added sequentially. Sequential detection of at least three epitopes could also occur if, for example, enzyme-labeled antibodies specific for each epitope are used, and the enzyme substrates are added one at a time in order to detect each epitope.

The first, second, or third binding agent of the method may detect an epitope that is the result of posttranslational modification, alternative splicing, or degradation.

Any method of the invention may also include repeating each of these steps with a second biological sample (from the same or different subjects) and comparing the component detected from the first biological sample to that detected in the second biological sample. The second biological sample may be obtained after a predetermined period of time after the first biological sample, may be obtained from the same or different subject than the first, and/or may be obtained from the same or different tissue than the first.

The methods of the invention may also be expanded for detection of more than three components or epitopes. Methods of the invention may also be employed in combination, where epitopes of one or more components of a complex are assayed.

In another aspect, the invention features a kit that includes a device having an immobilized binding agent on its surface in a pattern that generates a signal, wherein the immobilized binding agent is capable of binding to a biomarker complex. The kit also includes a detecting binding agent that specifically binds to a first component of the biomarker complex, a detecting binding agent that specifically binds to a second component of the biomarker complex, and a detecting binding agent that specifically binds to a third component of the biomarker complex. The detecting binding agents that specifically bind to the first, second, or third component of the biomarker complex do not specifically bind to any other component of the biomarker complex.

In another aspect, the invention features a kit that includes a device having an immobilized binding agent on its surface in a pattern that generates a signal, wherein the immobilized binding agent is capable of binding to a biomarker. The kit also includes at least three detecting binding agents that specifically bind to different epitopes of the biomarker.

An example of a biomarker or a component of a biomarker complex is a protein, a nucleic acid, a virus, or a cell. The amount, e.g., presence, absence, or concentration (relative or absolute), of a component of the biomarker complex present in a biological sample may be an indicator of a disease (e.g., myocardial infarction) in a subject, or the ratio (i.e., relative amount) between the components may be an indicator of a disease (e.g., myocardial infarction) in a subject. The presence, absence, or degree of posttranslational modification, alternative splicing, or degradation of a biomarker present in the biological sample may also be an indicator of a disease in a subject. The biomarker complex may be an immune complex or a troponin complex (e.g., a cardiac troponin complex). A biomarker, biomarker complex, or multiple biomarkers and biomarker complexes may be detected in a biological sample using the methods and kits described herein.

The binding agents of the invention may be an anti-TnI antibody (e.g., anti-cTnI antibody), an anti-TnT antibody (e.g., anti-cTnT antibody), or an anti-TnC antibody (e.g., anti-cTnC antibody). The signal may be the diffraction of light illuminating the device. Preferably, detection of binding to the device is by optical diffraction.

By "antibody" is meant monoclonal antibodies (including full-length monoclonal antibodies), polyclonal antibodies, multispecific antibodies (e.g., bispecific antibodies), and antibody fragments. An antibody specifically binds to an antigen. Exemplary antibodies include anti-cTnI antibody (e.g., 8I-7), anti-cTnT antibody (e.g., 1A11), and anti-cTnC antibody (e.g., 7B9).

By "antigen" is meant a molecule to which an antibody can selectively bind. The target antigen may be a protein, carbohydrate, nucleic acid, lipid, hapten, or other naturally occurring or synthetic compound. Preferably, the target antigen is a protein or a complex of proteins. Exemplary antigens include cardiac troponin (cTn) and the cardiac troponin components (cTnI, cTnT, and cTnC).

By "binding affinity" is meant the strength of the total noncovalent interactions between a single binding site of a molecule (e.g., an antibody) and its binding partner (e.g., an antigen). Unless indicated otherwise, as used herein, "binding affinity" refers to intrinsic binding affinity, which reflects a specific interaction between members of a binding pair (e.g., antibody and antigen). The affinity of a molecule X for its partner Y can generally be represented by the dissociation constant ($K_d$). Affinity can be measured by standard methods known in the art, including those described herein. Low-affinity antibodies generally tend to dissociate readily, whereas high-affinity antibodies generally tend to remain bound longer.

By "binding agent" or "detecting binding agent" is meant a molecule that has a binding affinity for another molecule. Binding agents include any substance capable of binding a biomarker, a biomarker complex, or a component thereof. The binding agent may be, e.g., a protein (e.g., an antibody, antigen, or fragment thereof) or a polynucleotide (e.g., an aptamer). Preferably, the binding agent specifically binds to only one component of the biomarker complex and not to any other components of the biomarker complex. Multiple binding agents may be used in the invention described herein to detect each component of a biomarker complex or multiple epitopes of a biomarker.

By "biological sample" is meant a sample obtained from an individual and used in a diagnostic or monitoring assay. Biological samples encompass, e.g., a clinical sample, cells in culture, cell supernatants, cell lysates, serum, plasma, biological fluid (e.g., urine), and tissue samples. The source of the biological sample may be solid tissue (e.g., from a fresh, frozen, and/or preserved organ, tissue sample, biopsy, or aspirate), blood or any blood constituents, bodily fluids (such as, e.g., urine, lymph, cerebral spinal fluid, amniotic fluid, peritoneal fluid, or interstitial fluid), or cells from any time in gestation or development of the individual. In some embodiments, the biological sample is obtained from a primary or metastatic tumor. The biological sample may contain compounds that are not naturally intermixed with the tissue in nature, such as preservatives, anticoagulants, buffers, fixatives, nutrients, or antibiotics.

By "biomarker" is meant a molecule, other chemical species (e.g., an ion), or particle that is an indicator of a biological (e.g., pathological or disease) state. Exemplary biomarkers include proteins (e.g., antigens or antibodies), carbohydrates, cells, viruses, nucleic acids, and small organic molecules. The biomarker may be a biomarker complex.

By "biomarker complex" is meant at least two components, e.g., molecules (e.g., proteins, nucleic acids, or carbohydrates), that associate noncovalently to form a complex. A biomarker complex may include 2, 3, 4, 5, 6, 7, 8, 9, 10, or more components. A complex may or may not be made up of a single type of component.

By "cancer" is meant the physiological condition in mammals that is typically characterized by unregulated cell growth. Included in this definition are benign and malignant cancers, as well as dormant tumors or micro-metastases. Examples of cancer include, but are not limited to, carcinoma, lymphoma, blastoma, sarcoma, and leukemia. More particular examples of such cancers include, e.g., prostate cancer, squamous cell cancer, small-cell lung cancer, non-small-cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, vulval cancer, thyroid cancer, hepatic carcinoma, gastric cancer, melanoma, and various types of head and neck cancer.

By "cardiovascular disease" is meant a disease that affects the heart and/or blood vessels (e.g., veins and arteries). Exemplary cardiovascular diseases include angina, myocardial infarction (e.g., acute myocardial infarction), cardiac amyloidosis, cardiac contusions, defibrillation, coronary vasospasms, dilated cardiomyopathy, heart failure, hypertrophic cardiomyopathy, myocarditis, atherosclerosis, or supraventricular tachycardia.

By "disease" is meant any condition that may be diagnosed or screened for according to the methods of the invention described herein. Non-limiting examples of diseases to be diagnosed herein include, e.g., cardiovascular diseases (e.g., myocardial infarction), cerebrovascular diseases (e.g., stroke), cancers (e.g., malignant tumors, carcinomas, blastomas, and sarcomas), autoimmune diseases (e.g., autoimmune hepatitis, multiple sclerosis, systemic lupus erythematosus, myasthenia gravis, type I diabetes, rheumatoid arthritis, psoriasis, Hashimoto's thyroiditis, Grave's disease, Sjogren's syndrome, and scleroderma), and infections (e.g., hepatitis C or human immunodeficiency virus (HIV) infections).

By "immobilized" is meant bound directly or indirectly to a surface of, e.g., a device, including attachment by covalent binding or noncovalent binding (e.g., hydrogen bonding, ionic interactions, van der Waals forces, or hydrophobic interactions).

By "posttranslational modification" is meant chemical modification of a protein after its translation. This includes, but is not limited to, the addition of functional groups (e.g., phosphorylation, glycosylation, acetylation, alkylation, methylation, formylation, oxidation, or biotinylation), addition of proteins or peptides (e.g., ubiquitination), changing the chemical nature of amino acids (e.g., deamination or demethylation), and structural changes (e.g., disulfide bridges or proteolytic cleavage).

By "signal" is meant light intensity (e.g., light generated by fluorescence, bioluminescence, or phosphorescence), ionizing radiation, particle emission, magnetism, staining, or a product of a reaction involving an enzyme. Diffraction, absorbance, polarization, reflection, deflection, increases, decreases, or amplification of a signal may be indicative of an event (e.g., binding of a biomarker or biomarker complex to an antibody immobilized on the surface of a diffraction-based device).

An antibody that "specifically binds" is an antibody or fragment thereof that recognizes and binds an antigen, but that does not substantially recognize or bind to other molecules in a biological sample. Specific recognition of an antigen by an antibody may be assayed by using, e.g., light diffraction devices with an immobilized capture surface or using standard techniques known to one of skill in the art, such as immunoprecipitation, Western blotting, and ELISA.

By "subject" is meant humans and other animals including, e.g., mice, rats, guinea pigs, hamsters, rabbits, cats, dogs, goats, sheep, cows, or monkeys.

By "troponin" is meant a protein complex found in skeletal or cardiac muscles involved in muscle contraction. Troponin (Tn) may be composed of three subunits: TnI, TnC, and TnT (FIG. 1). Cardiac troponins (cTn) may be modified during ischemic injury and are present in subjects with cardiovascular disease (e.g., myocardial infarction). A troponin complex may or may not contain all three subunits. A troponin complex may exist as a trimer, a dimer of any two of the subunits, a combination of trimer and dimer, or a combination of any single troponin subunit, dimer, and trimer. Any component of the troponin complex may be subjected to modification including, but not limited to, posttranslational modification, alternative splicing, or degradation.

Other features and advantages of the invention will be apparent from the following description, the drawings, and the claims.

BRIEF DESCRIPTION OF THE DRAWINGS

FIG. 9A is a graph showing a real-time trace of the capture of cTn and detection of cTnI. The bt-8I-7 antibody was immobilized on the surface of the device (black arrow). The cTn complex was captured (empty arrow), and anti-cTnI (the 3E3 antibody) detected the cTnI as part of the cTn complex (dashed arrow). All non-labeled portions are buffer wash. Spikes are air gaps separating each reagent. FIG. 9B is a graph showing a negative control of the experiment of FIG. 9A. BSA-milk (empty arrow) was used as the analyte instead of cTn in the otherwise identical experiment, as shown in FIG. 9A.

FIG. 10A is a graph showing the capture of cTn (empty arrow) by bt-8I-7 and detection of cTnI by an antibody specific for the N-terminus of cTnI (P3) (dashed arrow). FIG. 10B is a graph showing the capture of cTn (empty arrow) by bt-8I-7 and detection of cTnI by an antibody specific for the C-terminus of cTnI (MF4) (dashed arrow). FIGS. 10C and 10D are graphs showing negative controls of FIGS. 10A and 10B, respectively. BSA-milk (empty arrow) was used as the analyte instead of cTn.

FIG. 11A is a graph showing an avidin-immobilized bt-8I-7 (black arrow) captured cTn complex (cTnI-cTnT-cTnC, empty arrow). The presence of cTnI was confirmed using anti-cTnI MF4 antibody (dashed arrow). The presence of cTnT was detected with anti-cTnT (1A11) (black double arrow). FIG. 11B is a graph showing an analyte negative control of FIG. 11A. BSA-milk (empty arrow) was used instead of cTn. FIG. 11C is a graph showing an analyte control of (A). A cTnI (empty arrow) analyte was used (in the absence of cTnT) instead of cTn.

FIG. 12A is a graph showing an avidin-immobilized bt-8I-7 (black arrow) captured cTn complex (cTnI-cTnT-cTnC, empty arrow). The presence of cTnI was confirmed using anti-cTnI MF4 antibody (dashed arrow). The presence of cTnC was detected with anti-cTnC (7B9) (black double arrow). FIG. 12B is a graph showing an analyte negative control of FIG. 12A. BSA-milk (empty arrow) was used as the analyte instead of cTn. FIG. 12C is a graph showing an analyte control of FIG. 12A. A cTnI analyte (empty arrow) was used (in the absence of cTnT) instead of cTn.

FIG. 13A is a graph showing the detection of the cTnI-cTnC complex. HRP-7B9 antibody (anti-cTnC) and the AMI serum (premix) were pre-incubated at 4° C. overnight prior to adding to the device (empty arrow). Avidin-immobilized bt-8I-7 antibody (anti-cTnI, black arrow) captured the "cTn" complex. TMB amplified the detection of cTnC (dashed arrow). FIG. 13B is a graph showing a comparison of the TMB signals of the AMI patient serum and normal serum for the detection of cTnC. The "Normalized DI" is the ratio of TMB Diffractive Intensity (DI) to the maximal bt-8I-7 DI change. FIG. 13C is a graph showing the detection of a small amount of cTnT bound to cTnI (or cTnI-cTnC). HRP-1A11 (anti-cTnT, empty arrow) was used instead of HRP-7B9 in the otherwise identical experiment as FIG. 13A. FIG. 13D is a graph showing a comparison of the TMB signals of the AMI patient serum and normal serum for cTnT detection. FIG. 13E is a graph showing confirmation of the presence of cTnI in the cTn complex. HRP-3E3 (anti-cTnI, empty arrow) was used instead of HRP-7B9 in the otherwise identical experiment as FIG. 13A. FIG. 13F is a graph showing a comparison of the TMB signals of the AMI patient serum and normal serum for cTnI detection.

DETAILED DESCRIPTION OF THE INVENTION

Figure 1:
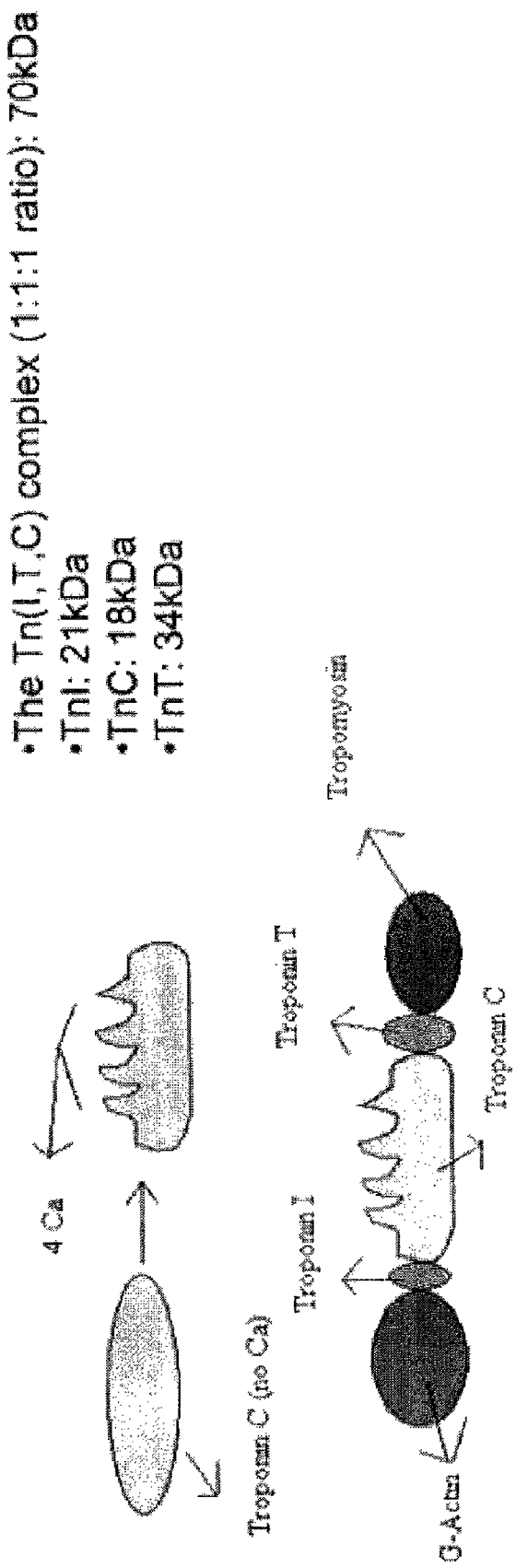
FIG. 1 is a schematic representation of the troponin complex in the presence and absence of calcium.

The invention features methods, devices, and kits for the detection of biomarkers and biomarker complexes and their components. The invention may be used for diagnosing disease and evaluating the efficacy of treatment.

In one embodiment, the methods of the invention include contacting a biological sample with a device having an immobilized binding agent on the surface of the device. The immobilized binding agent (e.g., an antibody) specifically binds to a biomarker complex (e.g., cardiac troponin), typically via a single component of the biomarker complex (e.g., cTnT, cTnC, or cTnI), whose binding is detectable. Additional binding agents that specifically recognize distinct components of the biomarker complex may then be introduced into the device to characterize the composition of the biomarker complex. The components may be detected using detection methods known to those skilled in the art (e.g., optical diffraction). In another embodiment, the methods of the invention include sequentially detecting epitopes of a biomarker in a biological sample by contacting the sample with a device having an immobilized binding agent on its surface in a pattern that generates a signal so that the biomarker in the sample specifically binds to the immobilized binding agent and contacting the biomarker with multiple binding agents that each specifically recognize an epitope of the biomarker.

Biomarkers, Biomarker Complexes, and Binding Agents

Exemplary biomarkers include proteins (e.g., antibodies or antigens), hormones, metabolites, polynucleotides and their analogs (e.g., DNA, RNA, or microRNA), lipids, toxins, or drugs, as well as larger assemblies, such as a virion or cell. The biomarker may be a complex, e.g., a cardiac troponin complex, a PSA-ACT complex, a CK-MB complex, a MRP8/MRP14 complex, or a MMP-2/TIMP-2 complex. The biomarker or biomarker complex may contain multiple epitopes. For example, the biomarker complex may be a multimer composed of single subunits, wherein the single subunits can be different isoforms that are modified, e.g., by alternative splicing, posttranslational modification, or degradation. Examples include protein forms that are cleaved, truncated (e.g., N-terminal or C-terminal truncations), phosphorylated, acetylated, alkylated, methylated, demethylated, formylated, or glycosylated. A complex may also be a population of isoforms of a single protein, wherein the isoforms may be modified as described herein. Exemplary multimeric complexes composed of single subunits are von Willebrand factor multimers. In addition, a sample may contain a mixture of multiple biomarkers that are not related, wherein the methods of the invention are used to detect the presence of each biomarker or biomarker complex. Alternatively, the biomarker may be a single molecule, e.g., protein, and the invention is used to detect the presence of multiple epitopes of the protein biomarker.

The biomarker or biomarker complexes or components thereof may be present in a biological sample (e.g., blood, serum, plasma, crude cell lysates, or urine).

A biomarker complex includes at least two components that are noncovalently associated. For example, the complex may contain 2, 3, 4, 5, 6, 7, 8, 9, 10, or more components. The components of the biomarker complex may include protein, nucleic acid, lipids, carbohydrates, cells, virions, or any combination thereof. An individual component may be modified as described herein.

The methods and kits of the present invention allow for the detection of each of the components of a biomarker complex or epitopes of a biomarker, e.g., for the diagnosis of a disease or monitoring the progression of a disease or therapy. The methods and kits of the present invention may also be used for antibody typing.

Various concentrations of biomarkers and biomarker complexes may be detected and measured by the methods described herein. Biomarkers present at concentrations less than, e.g., 100 milligrams/milliliter (mg/ml), 10 mg/ml, 1 mg/ml, 100 micrograms/milliliter (µg/ml), 10 µg/ml, 1 µg/ml, 100 nanograms/milliliter (ng/ml), 10 ng/ml, 1 ng/ml, 100 picograms/milliliter (pg/ml), 10 pg/ml, 1 pg/ml, 100 femtograms/milliliter (fg/ml), or 10 fg/ml may be detected in the biological sample, and the concentration may be measured.

Binding Agents

Binding agents include any substance capable of binding a biomarker, a biomarker complex, or a component of a biomarker complex. The binding agent may be, e.g., a protein (e.g., an antibody, antigen, or fragment thereof), carbohydrate, or a polynucleotide. The polynucleotide may possess sequence specificity for the biomarker, biomarker complex, or component of the biomarker complex or may be an aptamer.

An exemplary binding agent is an antibody that specifically binds to a biomarker, a biomarker complex, or a component of a biomarker complex. For example, the antibody may specifically bind to a troponin complex or a component of the troponin complex. The antibody may be, e.g., an anti-cTnC antibody, an anti-cTnI antibody, and/or an anti-cTnT antibody. The binding agent used in the invention will ultimately depend on the biomarker or biomarker complex being assayed. The number of binding agents used in the invention described herein may be 2, 3, 4, 5, 6, 7, 8, 9, 10, or more. The binding agents may be applied to the device of the invention sequentially for sequential probing of components or epitopes.

The number of binding agents used will typically depend on the number of components within a biomarker complex or the number of epitopes of a biomarker to be assayed. For example, to detect each component of the cardiac troponin complex, three binding agents (e.g., antibodies) may be used. In this example, bt-8I-7 (a biotinylated anti-cTnI antibody) may first be immobilized on the surface of a device as described herein, leading to the capture of the cTn complex on the surface of the device. Additional binding agents (e.g., antibodies) against each component of the cTn complex may then be introduced (e.g., in tandem or sequentially) to detect each component of the cTn complex. For example, the introduction of anti-cTnI antibody would lead to the detection of cTnI, introduction of anti-cTnC would lead to the detection of cTnC, and introduction of anti-cTnT would lead to the detection of cTnT. The introduction of binding agents against each component of the cTn complex allows for the characterization of the biomarker complex. The presence or absence of a component or multiple components of the biomarker complex may be indicative of a disease.

Multiple binding agents may also be used to detect different epitopes of a biomarker or a single component of a complex. The use of multiple binding agents for the detection of multiple epitopes may be used to detect, for example, cleavage, truncation, degradation, or posttranslational modifications of the component. For example, an antibody against the C-terminus of the component, an antibody against the N-terminus of the component, an antibody against the central region of the component, and/or an antibody against posttranslational modifications, alternative splicing, or degradation of the component may be used to detect and characterize the component of the complex.

Immobilized binding agents are present on the surface of the devices described herein. The immobilized binding agent may bind covalently or noncovalently to the surface of the devices by methods known to one of skill in the art, such as a biotin-avidin or biotin-streptavidin interaction, a Protein A interaction, a Protein G interaction, a goat anti-mouse Fc interaction, an amide bond, or through any other covalent or noncovalent interaction.

Exemplary immobilized binding agents used in the devices of the invention may be agents that are, e.g., magnetic, positively charged, negatively charged, polarized, or capable of forming temporary dipoles, hydrogen bonds, van der Waals forces, or hydrophobic interactions, so that the immobilized binding agent can bind to biomarkers in a sample by noncovalent means. Other immobilized binding agents include, e.g., charged polymers, hydrophobic polymers, and carbohydrates.

Methods to Detect and Measure a Biomarker or Biomarker Complex in a Biological Sample The signal produced upon the binding of a biomarker or biomarker complex to the device of the invention described herein may be detected or measured using any technique known in the art, including, e.g., optical diffraction. Exemplary techniques for detection are provided in, e.g., U.S. Pat. No. 6,991,938, hereby incorporated by reference.

Methods for using optical diffraction-based assays are known to those skilled in the art and described in, e.g., U.S. Pat. Nos. 7,008,794 and 7,314,749, U.S. Patent Application Publication No. 2006/0099649, and in Goh et al. ("Diffraction-Based Assay for Detecting Multiple Analytes," *Anal. Bioanal. Chem.* 374: 54-56, 2002), which are hereby incorporated by reference.

Diffraction-based assays can involve immobilizing a binding agent (e.g., a protein (e.g., an antibody) or nucleic acid) or a combination of multiple binding agents in a distinct pattern on the surface of a device. Binding agents for the same or different analytes may also be immobilized in distinct locations or assay spots (e.g., up to eight distinct locations or assay spots) on the surface of a device for simultaneous assays. The immobilized binding agents within each spot are not randomly distributed but are immobilized in a pattern (e.g., a series of parallel lines) that produces a diffraction pattern when illuminated with light (e.g., light with a wavelength in the range from the ultraviolet to the infrared, but preferably a coherent and collimated light beam from a laser (e.g. diode, He—Ne, Nd:YVO$_4$, or Argon-ion lasers)).

Once the binding agent is immobilized on the device, the sample to be assayed is introduced into the device (e.g., by flowing the sample through the device), allowing the biomarkers or biomarker complexes present in the sample to bind to their binding agent on the surface of the device. When a particular biomarker or biomarker complex is present in the biological sample being tested, the subsequent binding event between the biomarker and its binding agent is accompanied by a change in the local thickness of the surface of the device and/or in the local index of refraction. Both the change in thickness and the change in refractive index will alter the optical properties at the interface between the device and sample in regions where binding has taken place. Since the binding agents are present on the device in a predetermined pattern, light incident on the surface of the device will not be scattered uniformly but rather will be diffracted. In one embodiment of this invention, the patterned substrate is substantially non-diffracting, and the binding events result in observable diffraction. In another embodiment, the patterned surface of the device produces observable diffraction, but the binding events alter the intensity of the diffracted signal. The intensity of the diffraction signal may be used to generate real-time binding curves. In one embodiment, the illumination and diffracted beams never pass through the sample, which is particularly advantageous for the detection of proteins in complex biological samples.

Binding agents for different components of a biomarker complex may be sequentially introduced into a diffractive device for the detection of immunologically distinct subunits or epitopes of the complex in a single experiment. In addition, binding agents may be sequentially introduced into the device to detect multiple epitopes of a single biomarker. Binding agents may also be sequentially introduced into the device to detect multiple biomarkers present in a biological sample. The results from these binding events may all be shown on a single binding curve, where, for example, the presence, absence, or ratio of binding events may then be directly compared.

Since the diffraction-based detection of binding events is dependent on the pattern of the immobilized binding agents, an increase in signal occurs only when biomarkers or biomarker complexes bind selectively to those immobilized binding agents. Non-specific binding to the surface of the devices employed by the invention generally produces little or no change in the diffraction signal. This label-free characteristic of the invention enables the direct study of multiple biomarker epitopes or biomarker complex interactions in parallel, including, e.g., protein-protein interactions, nucleic acid-nucleic acid interactions, and nucleic acid-protein interactions. The methods of the invention also allow for the direct study of multiple biomarkers in a given biological sample.

The methods of the invention may measure direct binding of a binding agent to a biomarker epitope or indirectly measure binding of a binding agent to a biomarker epitope using an additional moiety to amplify the optical diffraction. Examples of additional moieties include enzymes (e.g., horseradish peroxidase and alkaline phosphatase) or a bead. Enzymes may amplify optical diffraction by acting on a substrate to cause precipitation of the substrate or binding of the substrate to the enzyme, binding agent, or target.

Detection of the diffraction signal depends on the source of illumination. The detector may be, e.g., a position-sensitive photodiode, a photomultiplier tube (PMT), a photodiode (PD), an avalanche photodiode (APD), a charged-coupled device (CCD) array, the unaided eye, a camera, a photographic plate, or any other imaging device. The detector may be attached to the appropriate accessories to provide power and enable signal collection and data processing.

Devices

The device used in a diffraction-based assay is typically a flow-through device. The patterns on the surface of the device may be created using microlithography, microcontact printing, inkjet writing, robotic spotting, dip pen nanolithography, nanolithography by atomic force microscopy, or near-field optical scanning lithography. The device may be made of any suitable material (e.g., a synthetic polymer (e.g., polystyrene), glass, metal, silicon, or semiconductor). Depending on the choice of material, the device employed may be disposable. An exemplary device is described in U.S. Pat. No. 7,314,749, hereby incorporated by reference.

The surface of the device may be coated with different immobilized binding groups known in the art. Immobilized avidin groups on the surface of the device may be used for high-affinity immobilization of biotinylated binding agents (e.g., biotinylated antigens, biotinylated antibodies, or biotinylated polynucleotides). For example, a biotinylated antigen that specifically binds to an antibody may be immobilized on the surface of an avidin-coated device. Protein G on the surface of the device may bind to the Fc region of immunoglobulin molecules, allowing oriented immobilization of antibodies as binding agents on the surface of the device. Goat anti-mouse-Fc (GAM-Fc)-coated surfaces bind to the Fc region of mouse antibodies, allowing oriented immobilization of binding agents, e.g., mouse antibodies, on the surface of the device employed by the invention.

Immobilized carboxylate groups on an amine-reactive surface may be used to covalently link binding agents (e.g., with amide bonds) to the device's surface via an amine-coupling reaction. Other exemplary reactive linking groups, e.g., hydrazines, hydroxylamines, thiols, carboxylic acids, epoxides, trialkoxysilanes, dialkoxysilanes, and chlorosilanes may be attached to the surface of the device, such that binding agents may form chemical bonds with those linking groups to immobilize them on the surface of the device.

Uses of the Invention

The invention described herein features methods for diagnosing disease and evaluating the efficacy of treatment of a subject with a disease. Physicians and researchers may use the methods of the invention described herein to detect biomarkers or biomarker complexes (e.g., cardiac biomarkers (e.g., troponins), tumor antigens, antibodies against tumor antigens, or lipoproteins), to diagnose or screen for disease (e.g., cardiovascular diseases (e.g., myocardial infarction), cancer, or autoimmune diseases), or to detect naturally occurring immune complexes in patient samples.

Diagnosis of Diseases

As discussed, the methods described herein may be used to diagnose diseases (e.g., myocardial infarction) in a subject. A physician or researcher may diagnose the disease based on, e.g., the presence, absence, or concentration (relative or absolute) of a biomarker or biomarker complex (or components thereof) indicative of the disease in a biological sample. The disease being diagnosed may be a cardiovascular disease (e.g., acute myocardial infarction), cerebrovascular disease (e.g., stroke), or cancer (e.g., a carcinoma, lymphoma, blastoma, sarcoma, or leukemia). More particular examples of such cancers include prostate cancer, squamous cell cancer, small-cell lung cancer, non-small-cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, vulval cancer, thyroid cancer, hepatic carcinoma, gastric cancer, melanoma, and various types of head and neck cancer. The disease may also be an autoimmune disease, e.g., autoimmune hepatitis, multiple sclerosis, systemic lupus erythematosus, myasthenia gravis, type I diabetes, rheumatoid arthritis, psoriasis, Hashimoto's thyroiditis, Grave's disease, Sjogren's syndrome, or scleroderma. The methods described herein may also be used to diagnose infections, e.g., viral infections, such as hepatitis C infection and human immunodeficiency virus (HIV) infection.

Monitoring the Efficacy of Treatment

The methods described herein may be used to monitor the efficacy of treatment of a disease of a subject. Such an evaluation includes obtaining at least one sample from the subject, e.g., before treatment begins and obtaining at least one sample from the subject at a later time, e.g., any time after commencement of the treatment (e.g., 1, 2, 3, 4, 5, or 6 days; 1, 2, or 3 weeks; 1, 2, 3, 4, 5, 6, 7, 8, 9, 10, or 11 months; or 1, 2, 3, 4, or 5 years after treatment has begun). The pre- and post-treatment samples may then be applied to a device containing an immobilized binding agent (e.g., an antibody) that is capable of specifically binding to a biomarker or biomarker complex (or component thereof) associated with the disease of the subject. The devices generate signals that may be evaluated to determine the presence, absence, or concentration (relative or absolute) of a particular component of the biomarker or biomarker complex. The efficacy of treatment may then be evaluated by comparing the composition of the biomarkers or biomarker complexes in each sample. For example, a decrease in the concentration of the biomarker or biomarker complex in the sample obtained after treatment had commenced may be an indication that the treatment of the disease is efficacious. Methods of the invention may also be used to monitor biomarkers or complexes in patients not undergoing treatment, e.g., to monitor disease progression.

The methods of the invention may also speed the detection of a biomarker or biomarker complex in a number of ways, including, e.g., quantifying biomarker concentration and purity, characterizing binding kinetics, determining specificity and cross-reactivity, optimizing biomarker concentrations, step times, buffers, and additive composition, monitoring assay performance and matrix effects, and multiplexing biomarkers with minimized interference.

EXAMPLES

Example 1

Sequential Detection of Troponin Subunits in a Captured Biomarker Complex

We describe a novel immunoassay for analyzing the composition of a cardiac troponin biomarker complex using diffractive optics technology.

Figure 3:
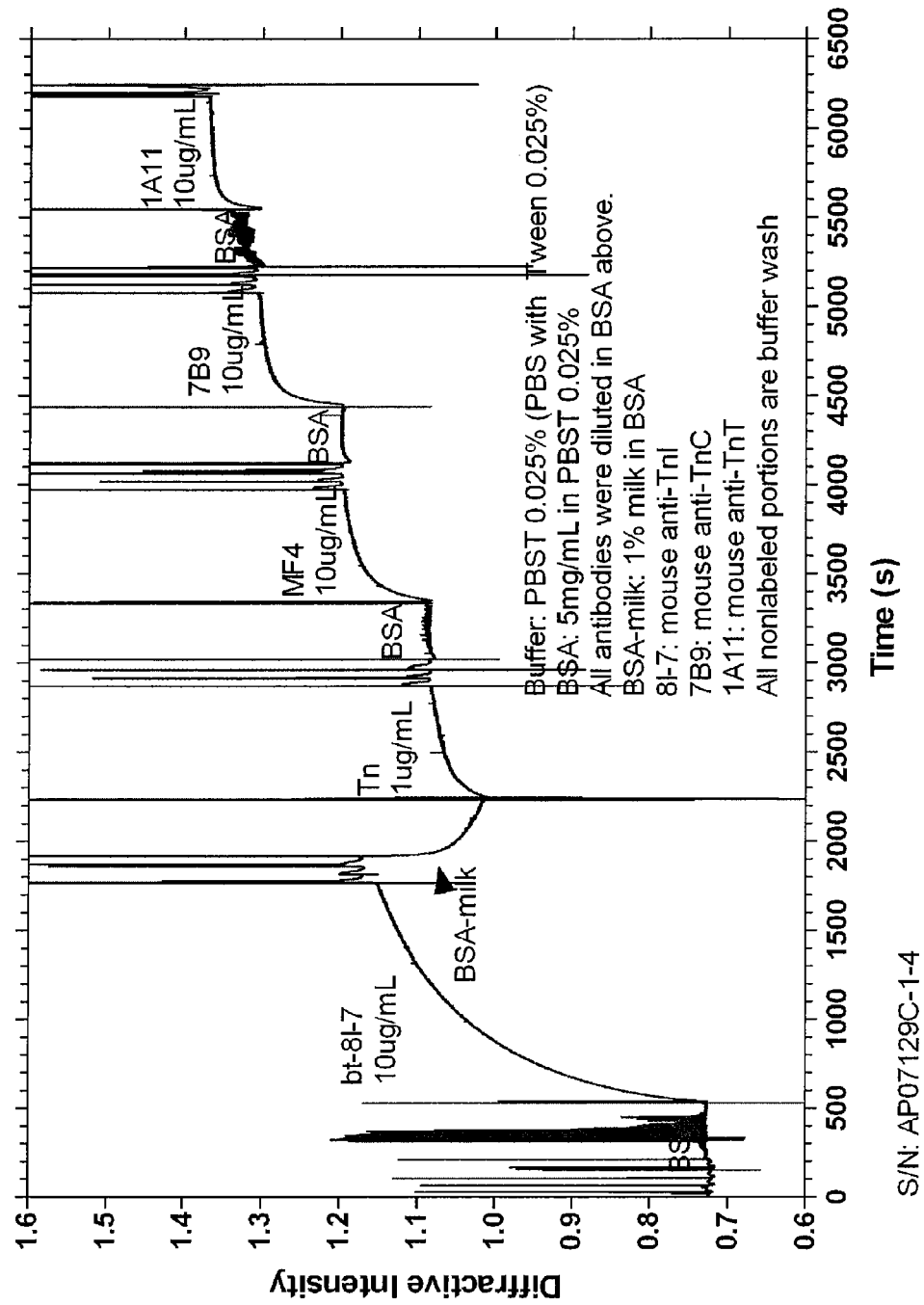
FIG. 3 is a graph showing sequential detection of the cTnI, cTnC, and cTnT subunits from cTn captured by biotinylated anti-cTnI antibody (bt-8I-7).

An anti-cTnI antibody, 8I-7 (Spectral Diagnostics, Inc., Canada), was immobilized on an avidin diffraction sensor device (a dotLab™ avidin device, Axela Inc., Canada). Binding was detected, indicated by an increase in the diffractive intensity (DI) (FIG. 3, Zone 1). A blocking buffer (a solution containing bovine serum albumin (BSA) and skim milk) was introduced into the device and allowed to incubate for several minutes. After the blocking step, a purified cardiac troponin complex (cTn) (Hytest Ltd., Turku, Finland) was contacted with the device at a concentration of 1 µg/ml. Binding was detected, indicated by an increase in the DI (FIG. 3, Zone 2). Upon introduction of a second cTnI specific antibody, MF4, a further increase in DI was observed (FIG. 3, Zone 3), indicating that the cTnI subunit was present in the complex. After a brief blocking step in a blocking solution containing BSA at a concentration of 5 mg/ml in a buffer containing PBS and 0.025% 2-[2-[3,4-bis(2-hydroxyethoxy)oxolan-2-yl]-2-(2-hydroxyethoxy)ethoxy]ethyldodecanoate (TWEEN-20®) (pH 7.4), the cTnC specific antibody, 7B9, was contacted with the device and a binding event was observed (FIG. 3, Zone 4), indicating that the cTnC subunit was present in the immobilized complex. Again, after a brief blocking step, the cTnT specific antibody, 1A11, was contacted with the device (FIG. 3, Zone 5), and a marked increase in the DI was observed, indicating that the cTnT subunit was present in this complex.

Figure 4:
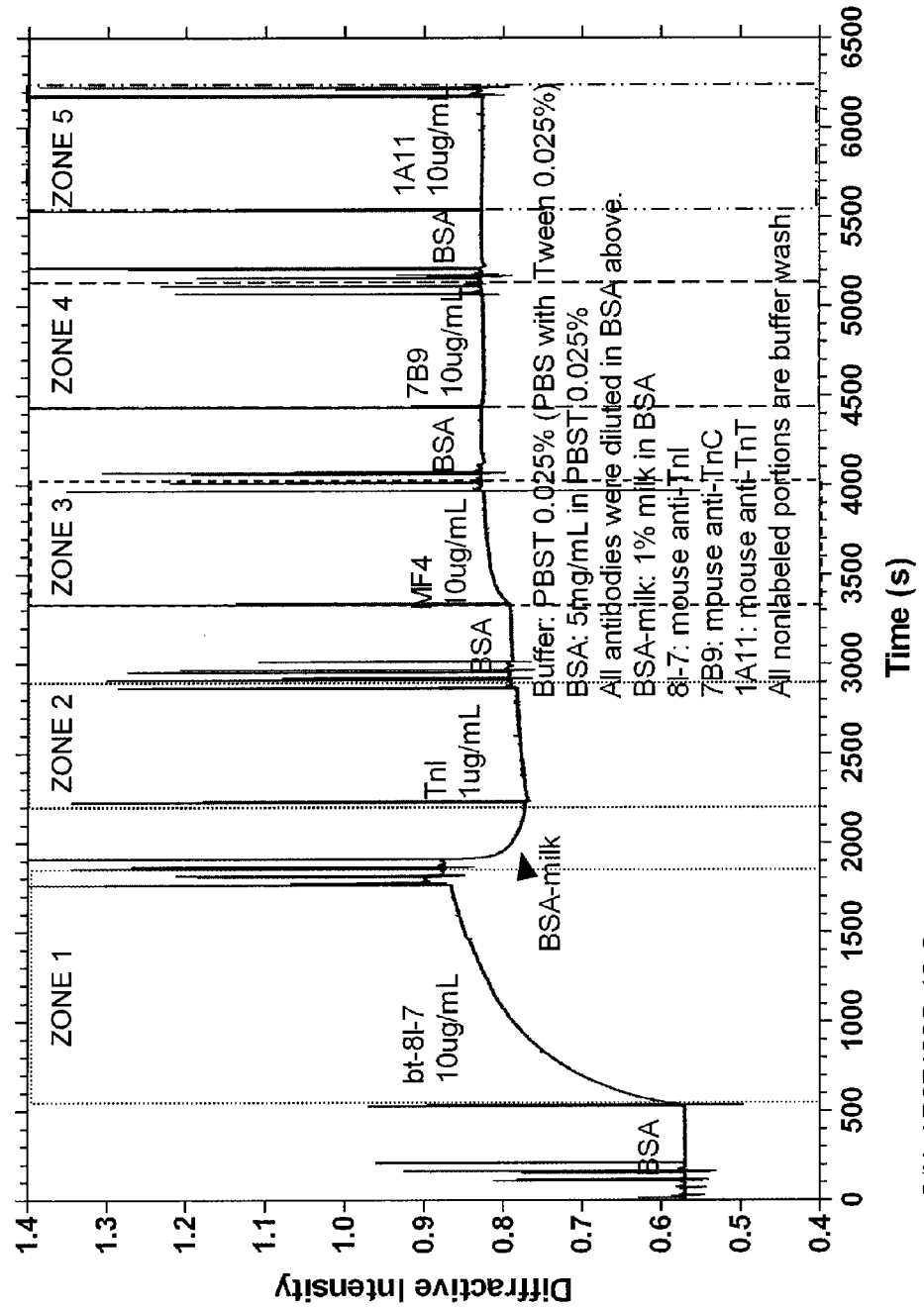
FIG. 4 is a graph showing detection of only cTnI (in the absence of cTnC and cTnT) when cTnI alone was the analyte.
Figure 5:
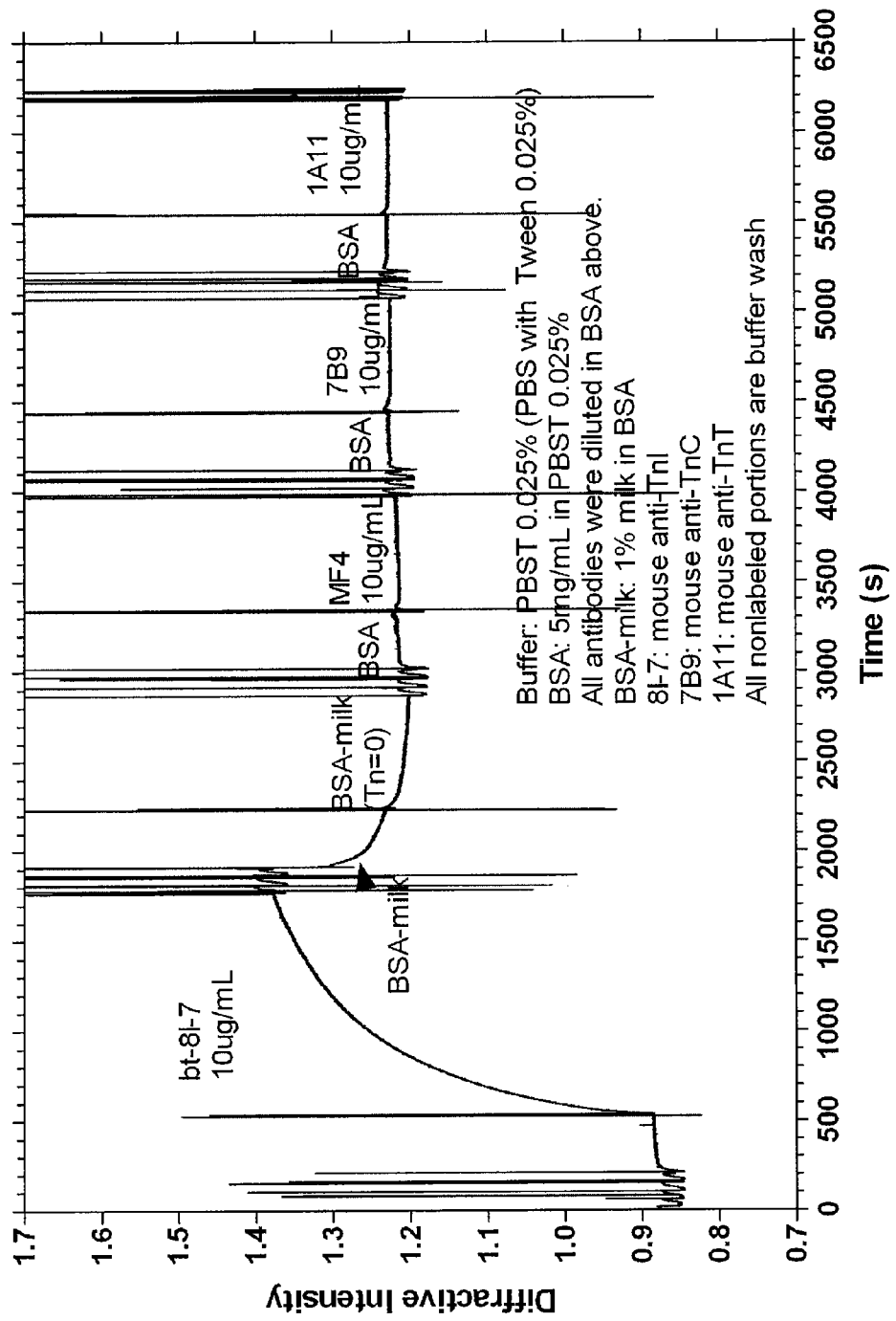
FIG. 5 is a graph showing that no detection of any of the cardiac troponin subunits was observed when the cardiac troponin complex was not present in a sample.

In order to eliminate the possibility that non-specific binding of the antibodies to each other was responsible for the observed binding events, we carried out two types of control experiments. As demonstrated in FIG. 4, we contacted the device with a sample that contained only the cTnI subunit (FIG. 4, Zone 2). As demonstrated in FIG. 5, we contacted the device with a sample without any cTn present in the buffer (FIG. 5, Zone 2). As expected, binding was detected in Zone 1 of FIG. 4 where the biotin moiety of bt-8I-7 led to its immobilization on the surface of the device and a visible increase in DI. cTnI bound to the device, as evidenced by the increase in DI (FIG. 4, Zone 2). Note that the DI change is dependent on the size of the antigen. Thus, a more modest increase in DI was expected upon cTnI binding, as cTnI is much smaller than the cTn complex containing all three subunits. MF4 bound readily to the captured cTnI, as indicated by the increase in DI (FIG. 4, Zone 3). However, no binding was observed when the 7B9 antibody (anti-cTnC; FIG. 4, Zone 4) or 1A11 antibody (anti-cTnT; FIG. 4, Zone 5) were contacted with the device, supporting the hypothesis that the binding events observed in FIG. 3 reflected specific binding to their target subunit and not non-specific binding to components in the assay system.

Finally, no detectable binding was detected when a control sample lacking cTn was contacted with the device (FIG. 5). Biotinylated bt-8I-7 bound to the avidin surface of the device, but antibodies against the cTnI, cTnC, and cTnT subunits of cTn failed to bind to the device (FIG. 5). These results corroborated our findings from the experiments of FIG. 4, and demonstrated that the MF4 binding events (FIGS. 3 and 4, Zone 3) were not due to non-specific binding to components of the assay system.

Example 2

Tandem Detection of Multiple Epitopes of cTnI Using Optical Diffraction

Figure 2:
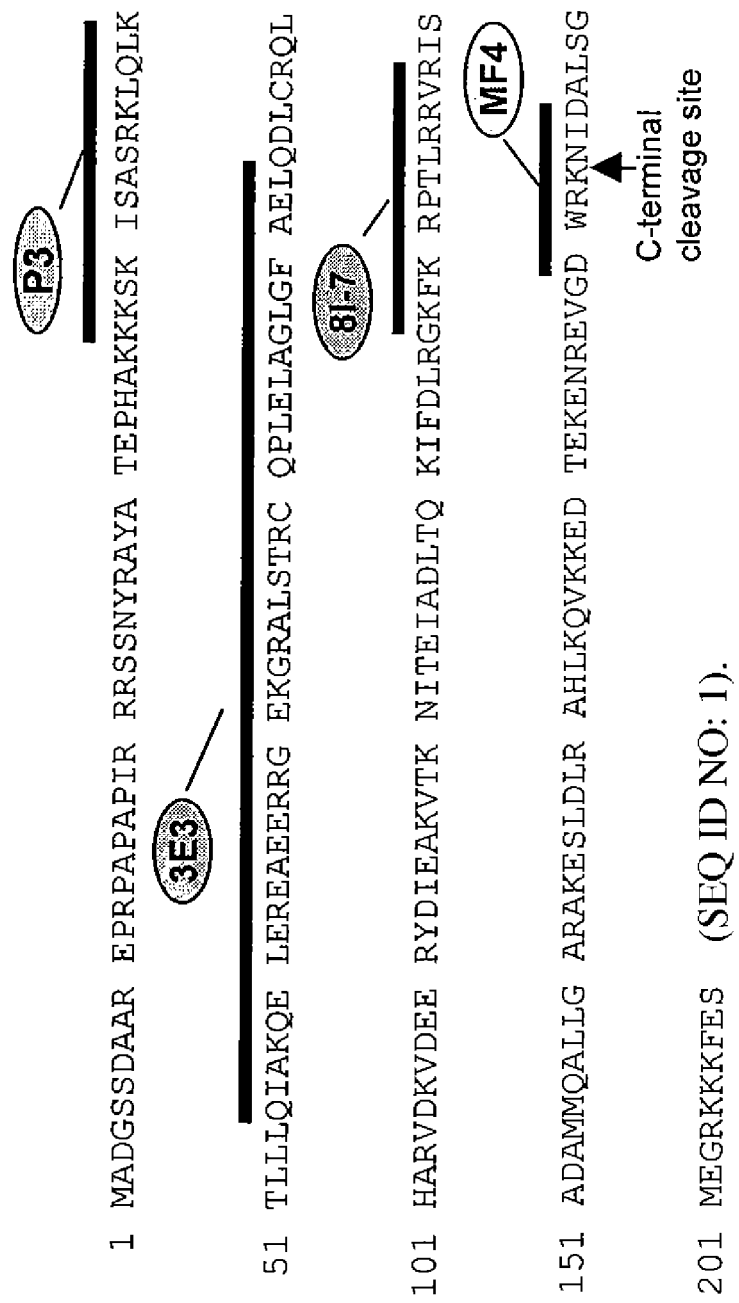
FIG. 2 is an epitope map of cTnI (SEQ ID NO: 1).

We describe a novel immunoassay for detecting multiple epitopes of a single subunit of a cardiac troponin biomarker complex using diffractive optics technology. In this example, individual monoclonal antibodies against four different epitopes of the cTnI protein were used in the immunoassay (FIG. 2).

Figure 6:
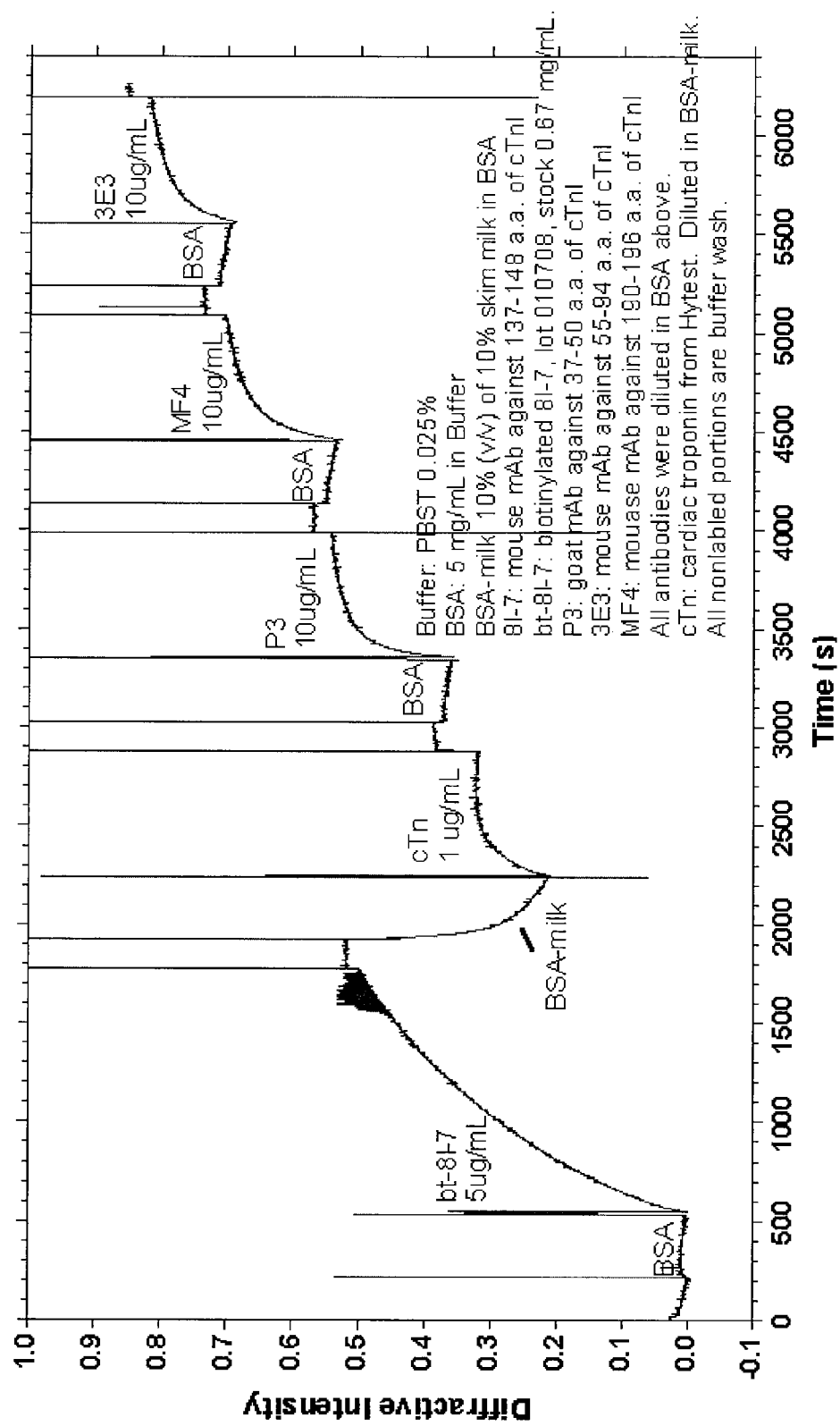
FIG. 6 is a graph showing the tandem detection of the N-terminus, C-terminus, and central region of cTnI using the cTn complex as an analyte.

A biotinylated anti-cTnI antibody, 8I-7 (Spectral Diagnostics, Inc., Canada), was immobilized on an avidin device (a dotLab™ avidin device, Axela Inc., Canada). Binding was detected, indicated by an increase in the diffractive intensity (DI) (FIG. 6). A blocking buffer (a solution containing bovine serum albumin (BSA) and skim milk) was introduced into the device and allowed to incubate for several minutes. After the blocking step, a purified cardiac troponin complex (cTn) (Hytest Ltd., Turku, Finland) was contacted with the device at a concentration of 1 µg/ml. Binding was detected, indicated by an increase in the DI (FIG. 6). A wash buffer was applied to the device (BSA in PBST). Following this wash step, P3 antibody (a monoclonal goat antibody against residues 37-50 of cTnI) (Biospecific, California, USA) was contacted with the device. Binding was detected, indicated by an increase in the DI (FIG. 6). Again, the device was washed using BSA in PBST. After this wash step, MF4 antibody (a monoclonal mouse antibody against residues 190-196 of cTnI) (Hytest Ltd., Turku, Finland) was added to the device, and a further increase in DI was observed (FIG. 6). After a final wash, 3E3 antibody (a monoclonal mouse antibody against residues 55-94 of cTnI) (Spectral Diagnostics, Inc., Canada) was added to the device and a further increase in DI was observed (FIG. 6). The above steps were repeated using cTnI as the analyte in lieu of the entire cTn complex (FIG. 7), and similar results were observed. As a negative control, the above steps were repeated using BSA-milk as the analyte (FIG. 8). No detectable binding was observed when BSA-milk was used as the analyte.

Figure 7:
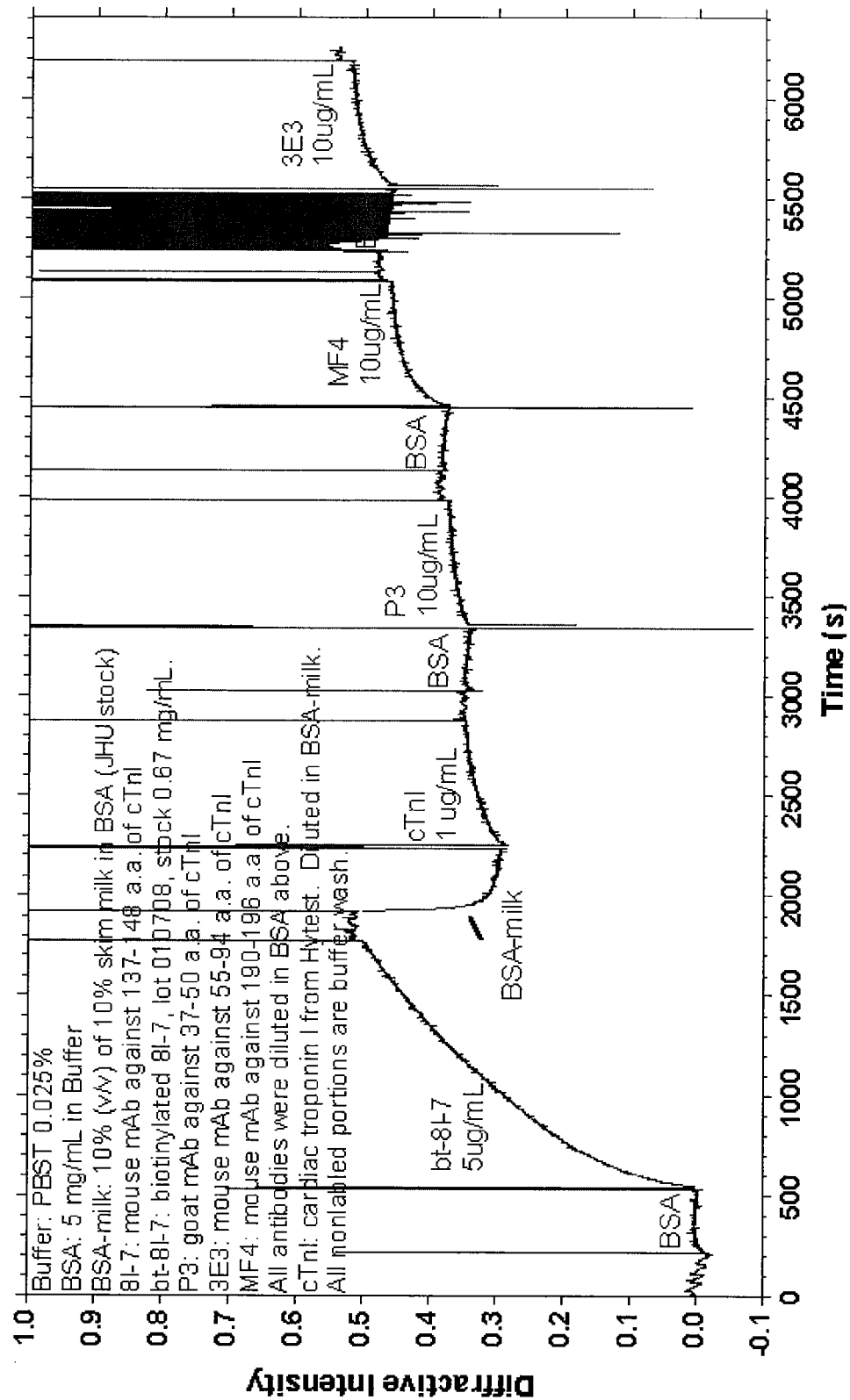
FIG. 7 is a graph showing the tandem detection of the N-terminus, C-terminus, and central region of cTnI using cTnI as an analyte.
Figure 8:
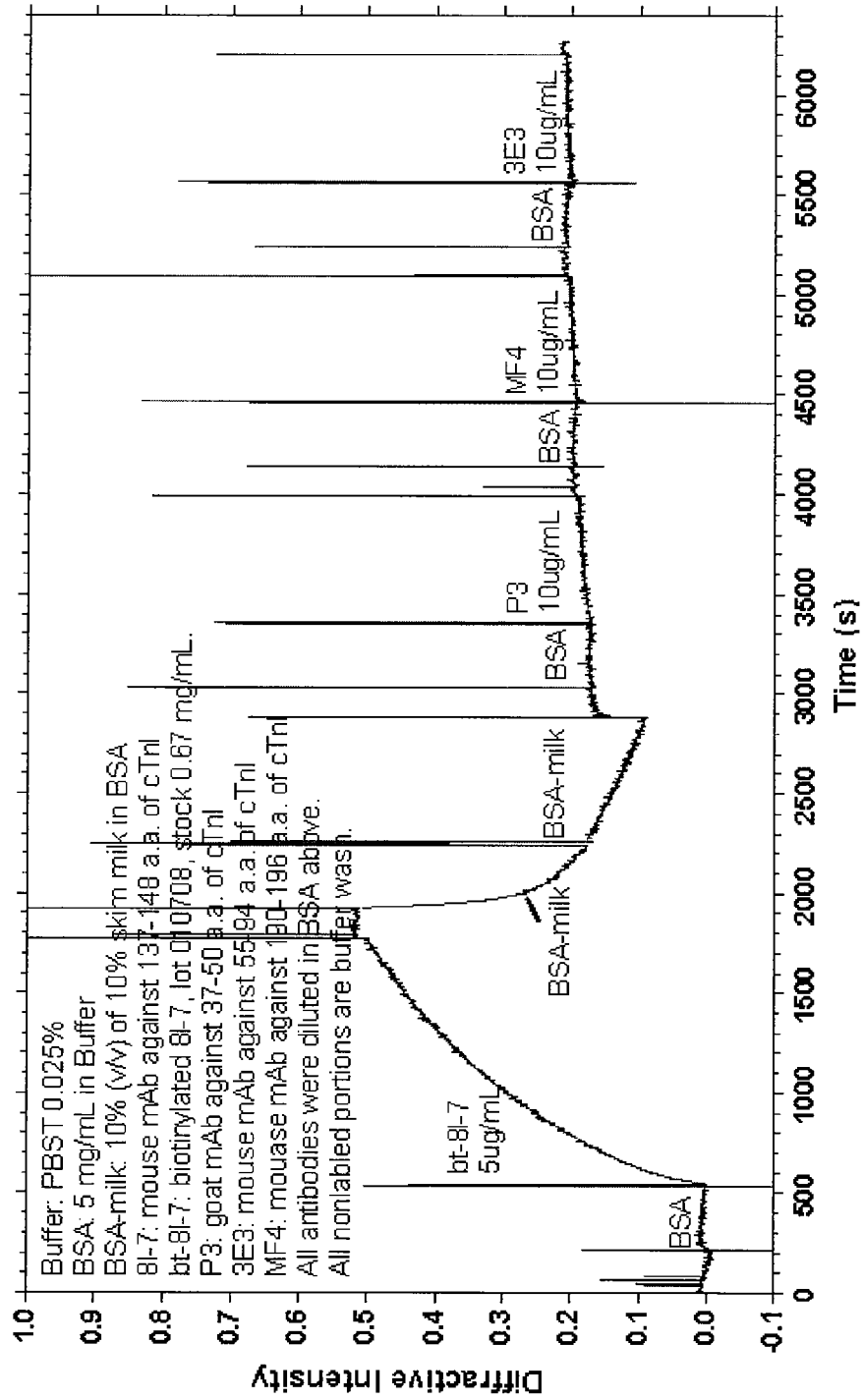
FIG. 8 is a graph of a negative control using BSA-milk instead of cTnI as the analyte.

As demonstrated in FIGS. 6 and 7, the bt-8I-7 antibody captured the cTnI subunit alone or as part of the cTn complex. Sequentially introduced antibodies against the N-terminus, C-terminus, and central region of cTnI detected the presence of their respective epitopes. Each step of antibody probing (i.e., each binding event from the binding of each detecting antibody) was performed in one experiment, and the results from all binding steps were shown in one binding curve, allowing a direct comparison of the results of each sequential addition.

Example 3

Characterization of the Primary and Ternary Structure of the Circulating Form of Cardiac Troponin In this example, cTnI was captured using a biotinylated anti-cTnI antibody that specifically binds to the constant region (residues 137-148). The anti-cTnI antibody was immobilized on a pre-patterned avidin sensor and probed with antibodies to either or both the N- and C-termini to determine if cTnI was degraded, or, alternatively, the sensor was probed sequentially with anti-cTnT and/or anti-cTnC antibodies to determine whether cTnI existed as a monomer, dimer, or trimer.

Figure 11:
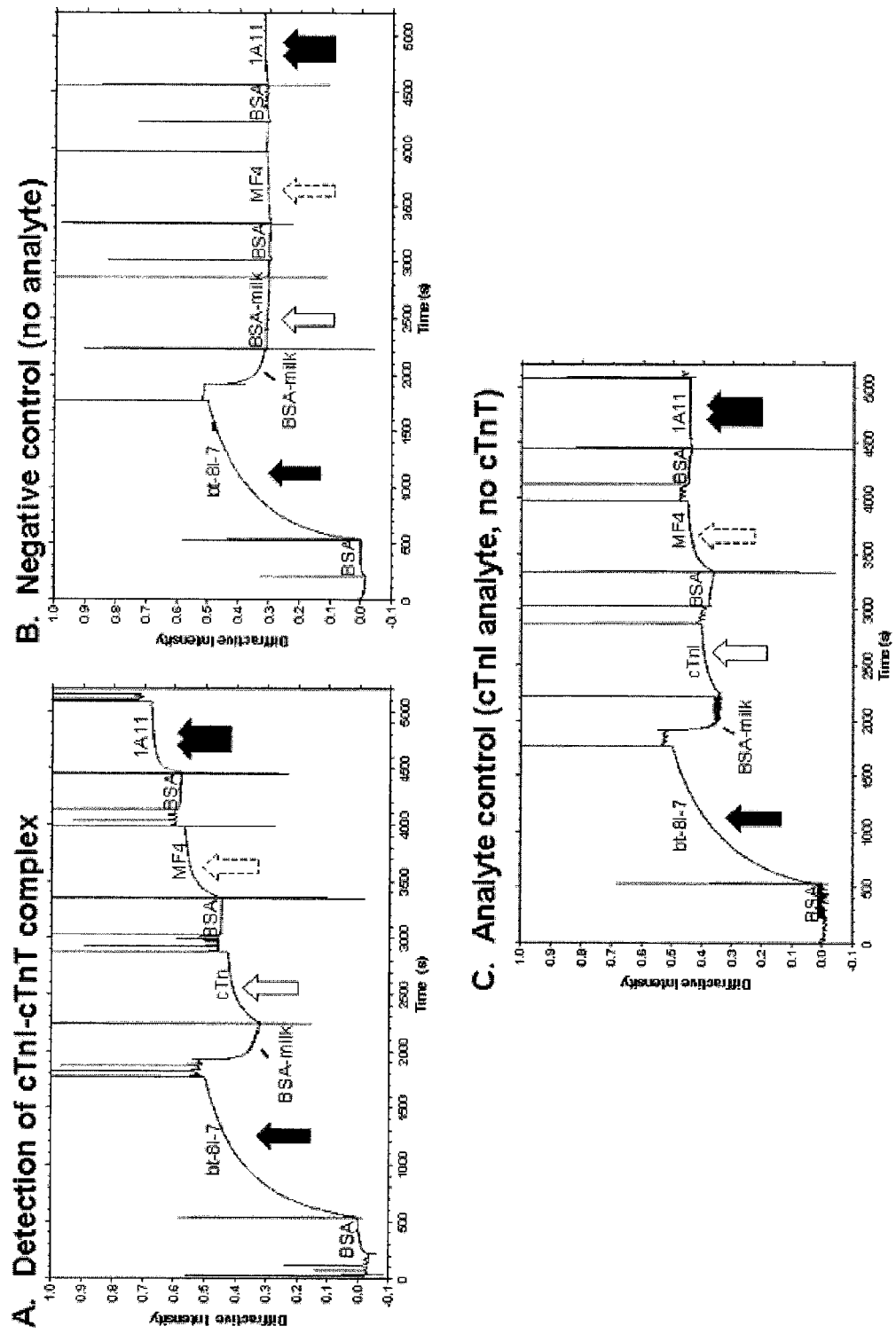
FIG. 11 shows the detection of the protein complex cTnI-cTnT.
Figure 12:
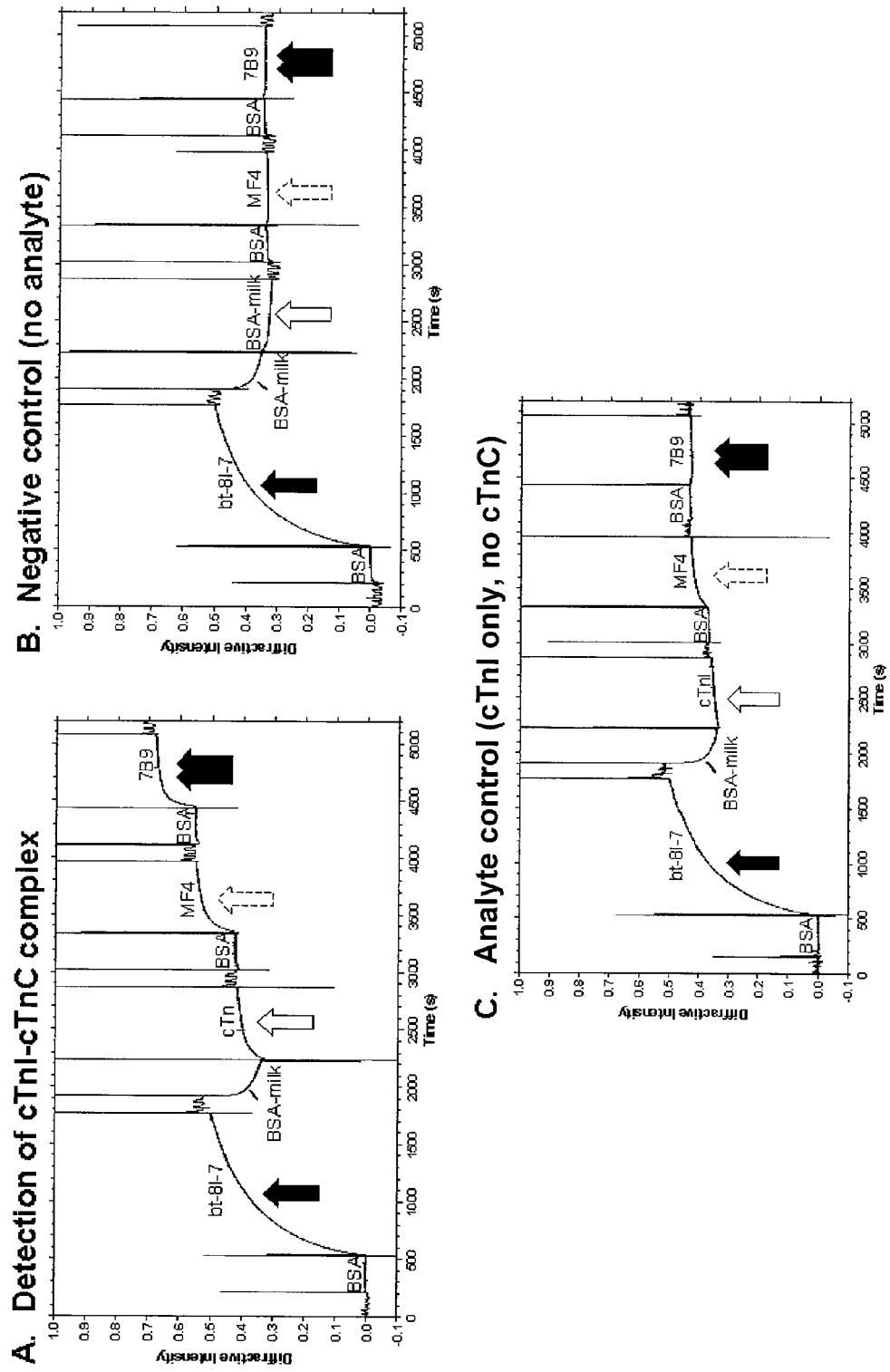
FIG. 12 shows the detection of the protein complex cTnI-cTnC.

The assays were performed in a dotLab™ device (optical diffraction device with an immobilized capture surface) with avidin surface chemistry (Axela Inc., Canada). All experiments were carried out using the dotLab™ device and real-time binding curves were recorded accordingly. Sequential sandwich immunoassays were performed. For each experiment, running buffer (PBS with 0.025% 2-[2-[3,4-bis(2-hydroxyethoxy)oxolan-2-yl]-2-(2-hydroxyethoxy)ethoxy]ethyldodecanoate (TWEEN 20®) pH 7.4) was introduced into the dry avidin sensors for 200 seconds to stabilize the flow system of the device and remove preservatives. BSA blocking buffer (5 mg/ml of BSA in running buffer) was introduced and incubated in the device for 5 minutes in mixing mode (e.g., repeatedly reversing flow directions within the sensor), a mode used in all subsequent incubations. Biotinylated 8I-7 antibody (10 µg/ml) was introduced and incubated in the device for 20 minutes. The 8I-7 antibody was biotinylated using FluoReporter Mini-Biotin-XX Protein Labeling Kit (Invitrogen, California, USA). The sensor was washed with running buffer. A BSA-milk blocking buffer (4.5 mg/ml of BSA and 1% of non-fat milk in running buffer) was introduced and incubated in the device for 5 minutes. Analyte (cTn or cTnI) at a concentration of 1 µg/ml or a serum sample was introduced and incubated in the device for 10 minutes. The sensor was washed with running buffer prior to a 5-minute incubation with the BSA blocking buffer. A detector antibody (10 µg/ml) was introduced and incubated in the device for 10 minutes. The sensor was washed at the end of run, or BSA and another detecting antibody were introduced and the cycle above repeated. In the first experiment (FIG. 9), cTnI was used as the analyte and was detected with 3E3 antibody. In the second experiment (FIG. 10), the integrity of the cTnI analyte was characterized using P3 and MF4 as the detecting antibodies. In the third experiment (FIG. 11), a cTn complex was used as the analyte, cTnI was detected with MF4 detecting antibody, and cTnT was detected with 1A11 detecting antibody. In the fourth experiment (FIG. 12), a cTn complex was used as the analyte, cTnI was detected with MF4 detecting antibody, and cTnC was detected with 7B9 detecting antibody.

Figure 13:
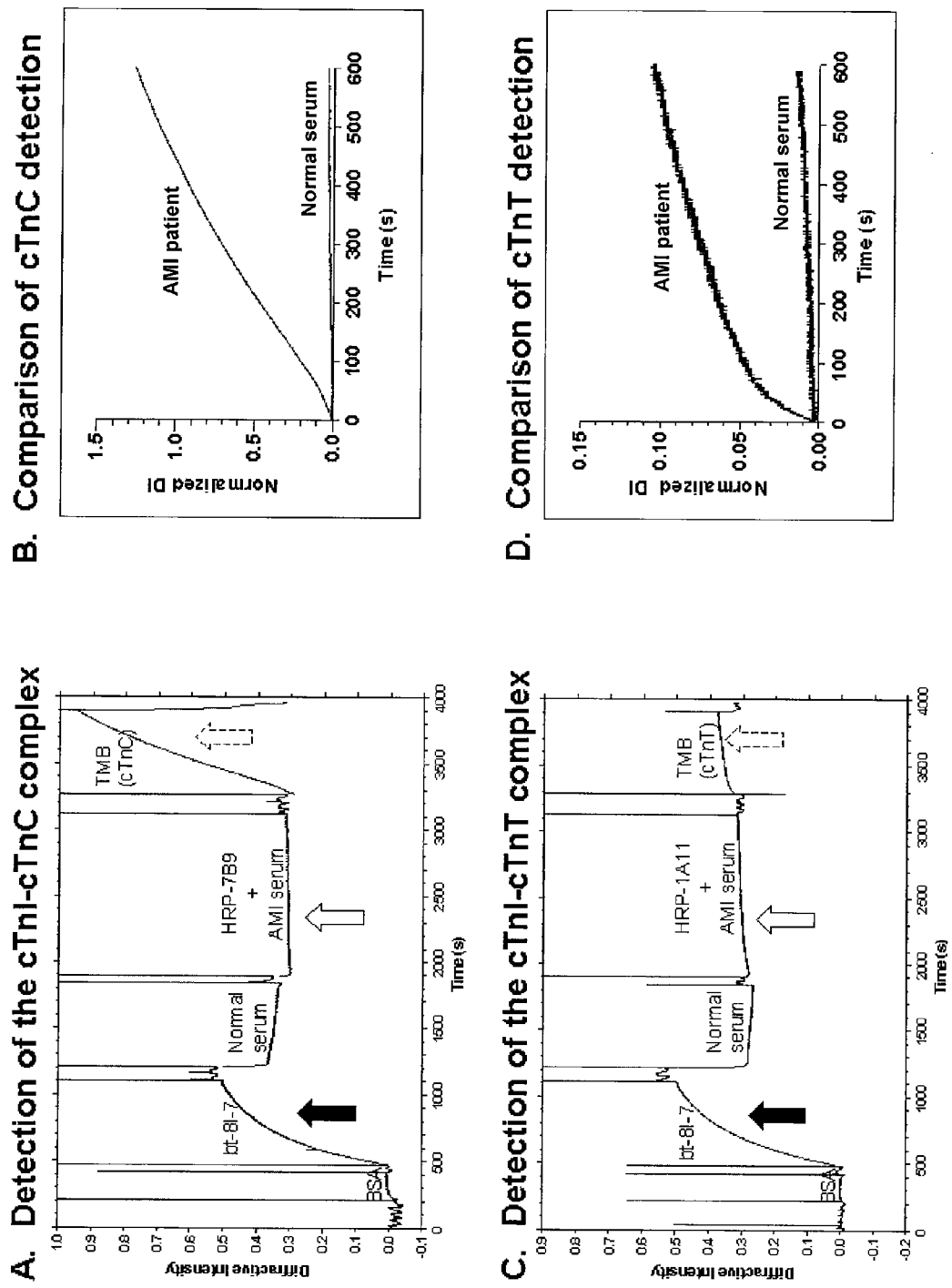
FIG. 13 shows the detection of the cTnI-cTnC and cTnI-cTnT complexes in serum from an acute myocardial infarction (AMI) patient.

A TMB amplified assay was performed for the detection and characterization of cTn in serum from a patient with acute myocardial infarction (AMI). The 3E3, 1A11, and 7B9 antibodies were labeled with horseradish peroxidase (HRP) using SureLink™ HRP Conjugation Kit (KPL Inc., Maryland, USA). A premix containing the horseradish-peroxidase-conjugated detector antibody (4 µg/ml) and 10% (v/v) AMI patient serum was pre-incubated offline at 4° C. overnight. The device was washed, blocked, and introduced with capture antibody (bt-8I-7) (5 µg/ml, 10 minutes), as described in the sequential sandwich immunoassay above. The premix containing the detector antibody and serum sample, which had been incubated offline, was introduced into the device and incubated for 20 minutes. The device was washed with the running buffer and PBS buffer. Finally, TrueBlue™ TMB (KPL Inc., Maryland, USA), a precipitating form of the peroxidase substrate, was introduced into the device and incubated for 10 minutes in static mode. In this experiment, the presence of cTnC in the cTnI-cTnC complex and the presence of cTnT in the cTnI-cTnT complexes were detected with HRP-7B9 and HRP-1A11, respectively (FIG. 13).

All data recorded in dotLab™ software were exported as a csv file and analyzed by GraphPad Prism (GraphPad Software Inc., California, USA).

Figure 9:
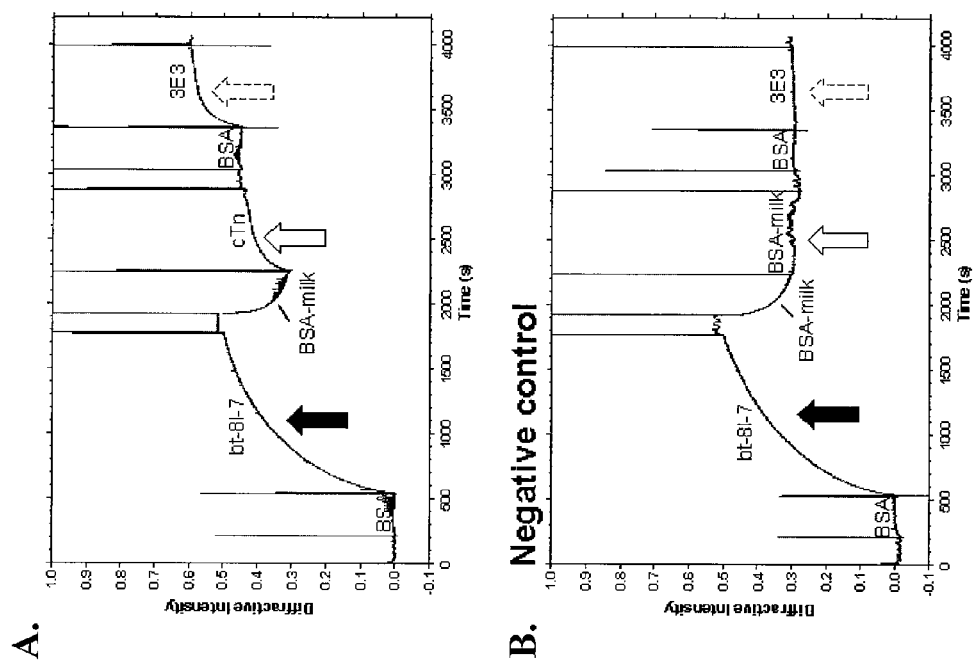
FIG. 9 shows the detection of cTnI using optical diffraction.
Figure 10:
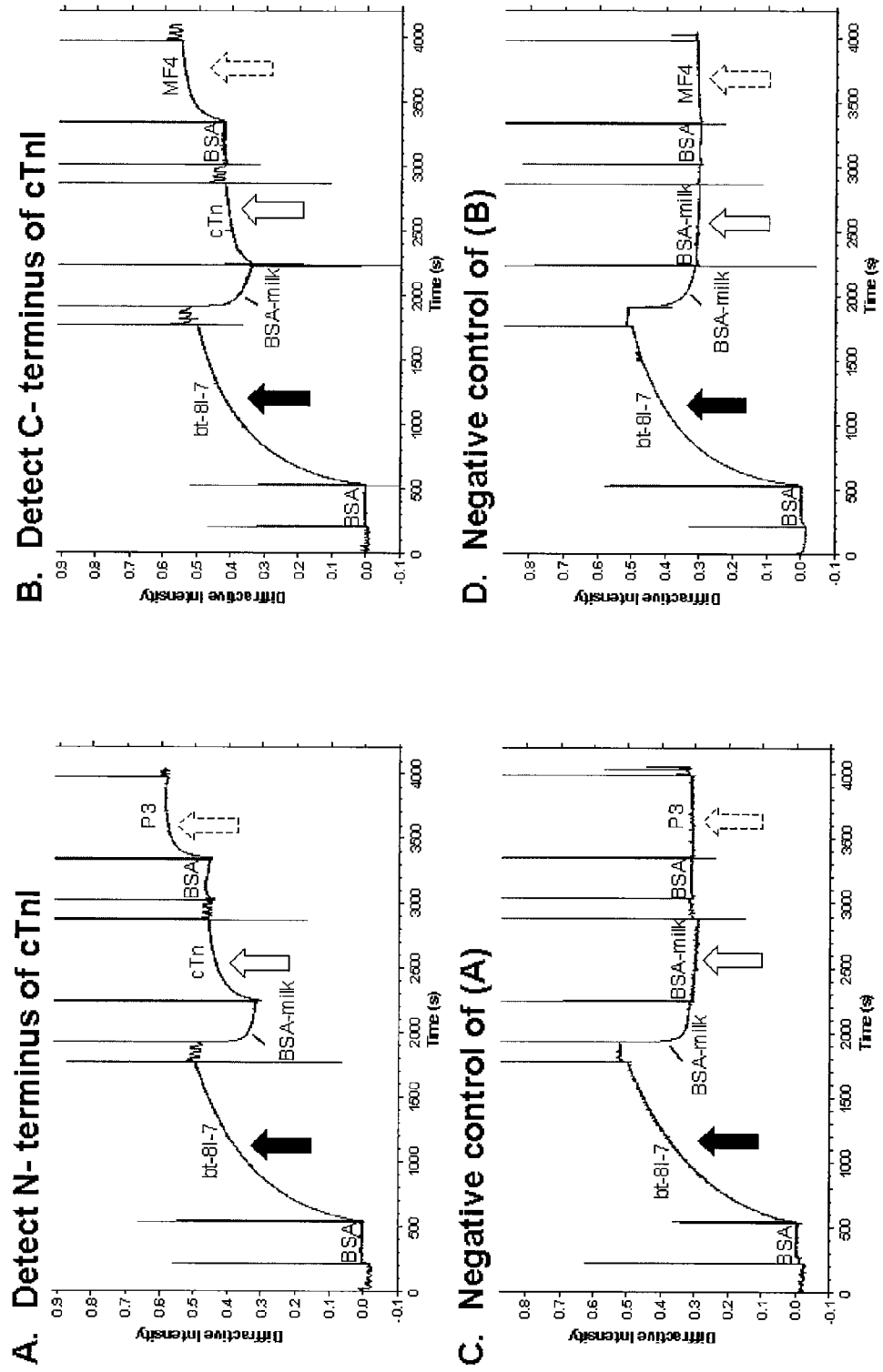
FIG. 10 shows the characterization of cTnI integrity.

The data show that the immunoassay was able to probe the integrity of cTnI (see, e.g., FIGS. 9 and 10). The N- and C-termini of cTnI were detected using different antibodies (FIG. 10); each antibody bound to the complex, indicating that the cTnI protein had retained its N- and C-termini. The immunoassays were also able to detect individual components of a cTn complex (see, e.g., FIGS. 11 and 12). In addition, the immunoassay was used to detect cTnI bound to cTnC and cTnT from serum obtained from an AMI patient, indicating that the dimer or intact cTn (cTnI-cTnT-cTnC) was present (FIG. 13).

Example 4

Sequential Determination of an Antibody Isotype Profile

In this example, biotinylated recombinant NIE protein (Ravi et al., *Mol. Biochem. Parasitol.* 125: 73-81 (2002)) was immobilized on a dotLab™ device and probed with NIE-specific antibodies. Five antibodies against specific human isotypes were sequentially added to the device to determine the isotype profile of the NIE-specific antibody.

All assays were performed on the dotLab™ device using avidin sensors and a running buffer of PBS with 0.05% 2-[2-[3,4-bis(2-hydroxyethoxy)oxolan-2-yl]-2-(2-hydroxyethoxy)ethoxy]ethyldodecanoate (TWEEN-20®) containing 10% v/v SeaBlock (Pierce). All washes were performed at a flow rate of 2000 μl/min, and all sample/reagent incubations were performed at a flow rate of 100 μl/min.

Figure 14:
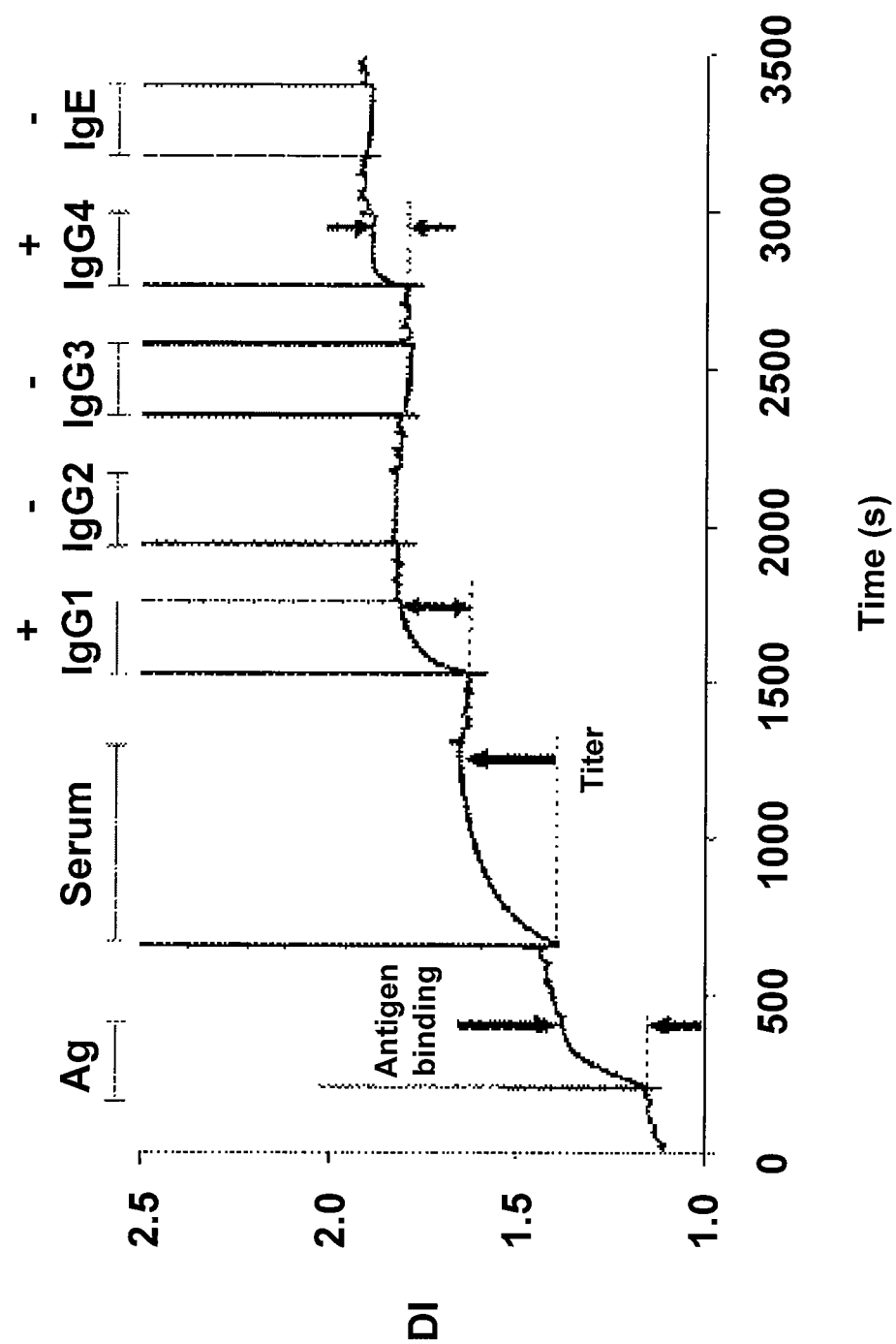
FIG. 14 is a graph showing the sequential determination of an antibody isotype profile. Biotinylated recombinant NIE protein (Ravi et al., *Mol. Biochem. Parasitol* 125: 73-81 (2002)) was immobilized on a diffraction-based sensor (a dotLab™ device, Axela Inc., Canada) and probed with NIE-specific antibodies. Five antibodies against specific human isotypes were sequentially added to the device to determine the isotype profile of the NIE-specific antibody. IgG1 and IgG4 bind the NIE-specific antibodies, and IgG2, IgG3, and IgE do not bind.

Following a series of washes with the running buffer to wet the surface of the device, 5 μg/ml of biotinylated recombinant NIE protein (a Strongyloides antigen) was applied to the device and incubated for 4 minutes. The device was washed briefly with running buffer. The device was then incubated with a Strongyloides-infected patient serum sample (10% v/v in running buffer) for 10 minutes containing NIE-specific antibodies. This incubation yielded an NIE-specific antibody binding curve (FIG. 14). To determine the isotype composition of the captured antibodies, the sensor was probed sequentially for 3 minutes each with antibodies against human isotypes IgG 1, IgG2, IgG3, IgG4, and IgE at a concentration of 10 μg/ml diluted in running buffer with brief washes between each incubation.

The data show (FIG. 14) that IgG1 and IgG4 bind the NIE-specific antibodies, and IgG2, IgG3, and IgE do not bind the NIE-specific antibodies. Similar methods may be used to characterize positive serological tests (e.g., acute versus chronic infection using IgM versus IgG isotype determination), to characterize antibody isotypes for the production of monoclonal antibodies, and to characterize immune responses for the development of vaccines.

Other Embodiments

All publications, patents, and patent applications mentioned in the above specification are hereby incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:

1. A method of detecting components of a biomarker complex in a biological sample, said method comprising:
   (a) contacting said biological sample with a device having an immobilized binding agent on the surface thereof in a pattern that generates a signal so that said biomarker complex in said sample specifically binds to said immobilized binding agent, wherein said biomarker complex comprises a first component, a second component, and a third component;
   (b) contacting said surface with a first detecting binding agent, wherein said first detecting binding agent specifically binds to said first component of the biomarker complex and not to said second or third component of the biomarker complex;
   (c) detecting said first component by a change in signal produced by said pattern upon binding of said first detecting binding agent to said first component;
   (d) contacting said surface with a second detecting binding agent, wherein said second detecting binding agent specifically binds to said second component of said biomarker complex and does not specifically bind to said first or third component;
   (e) detecting said second component by a change in signal produced by said pattern upon binding of said second detecting binding agent to said second component;
   (f) contacting said surface with a third detecting binding agent, wherein said third detecting binding agent specifically binds to the third component of said biomarker complex and does not specifically bind to said first or second component; and
   (g) detecting said third component by a change in signal produced by said pattern upon binding of said third detecting binding agent to said third component.

2. The method of claim 1, wherein said first component comprises a protein, a nucleic acid, a virus, or a cell.

3. The method of claim 1, wherein said biomarker complex is an immune complex.

4. The method of claim 1, wherein said biomarker complex is a troponin complex.

5. The method of claim 4, wherein said troponin complex is a cardiac troponin complex.

6. The method of claim 1, wherein said immobilized binding agent is an anti-TnI antibody, an anti-TnT antibody, or an anti-TnC antibody.

7. The method of claim 1, wherein said first detecting binding agent is an anti-TnI antibody, an anti-TnT antibody, or an anti-TnC antibody.

8. The method of claim 7, wherein said anti-TnI antibody is anti-cTnI antibody; said anti-TnT antibody is anti-cTnT antibody; or said anti-TnC antibody is anti-cTnC antibody.

9. The method of claim 1, wherein said second detecting binding agent is an anti-TnI antibody, an anti-TnT antibody, or an anti-TnC antibody.

10. The method of claim 1, wherein said third detecting binding agent is an anti-TnI antibody, an anti-TnT antibody, or an anti-TnC antibody.

11. The method of claim 1, wherein said signal is diffraction of light illuminating said device.

12. The method of claim 1, comprising repeating steps (a)-(c) with a second biological sample and comparing the first component detected from the first biological sample to that detected in the second biological sample.

13. The method of claim 1, comprising repeating steps (a)-(e) with a second biological sample and comparing the second component detected from the first biological sample to that detected in the second biological sample.

14. The method of claim 1, comprising repeating steps (a)-(g) with a second biological sample and comparing the third component detected from the first biological sample to that detected in the second biological sample.

15. The method of claim 12, wherein said second biological sample is obtained at a predetermined period of time after said first biological sample.

* * * * *